(12) United States Patent
Dejima

(10) Patent No.: US 9,610,129 B2
(45) Date of Patent: *Apr. 4, 2017

(54) MEDICAL MANIPULATOR

(71) Applicant: OLYMPUS CORPORATION, Tokyo (JP)

(72) Inventor: Takumi Dejima, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 299 days.

This patent is subject to a terminal disclaimer.

(21) Appl. No.: 14/246,762

(22) Filed: Apr. 7, 2014

(65) Prior Publication Data
US 2014/0222024 A1    Aug. 7, 2014

Related U.S. Application Data

(63) Continuation of application No. 13/155,793, filed on Jun. 8, 2011, now Pat. No. 8,808,277, which is a
(Continued)

(51) Int. Cl.
*A61B 17/28* (2006.01)
*A61B 19/00* (2006.01)
(Continued)

(52) U.S. Cl.
CPC ........ *A61B 19/22* (2013.01); *A61B 17/00234* (2013.01); *A61B 17/29* (2013.01);
(Continued)

(58) Field of Classification Search
CPC ... A61B 17/29; A61B 17/00234; A61B 19/22; A61B 2017/00318;
(Continued)

(56) References Cited

U.S. PATENT DOCUMENTS 4,919,112 A    4/1990 Siegmund
5,842,993 A    12/1998 Eichelberger et al.
(Continued)

FOREIGN PATENT DOCUMENTS

JP    2002-306494 A    10/2002
JP    2005-296412 A    10/2005
(Continued)

OTHER PUBLICATIONS

European Search Report dated Mar. 16, 2012 from corresponding European Patent Application No. EP 10 83 5768.2.
(Continued)

*Primary Examiner* — Gary Jackson
*Assistant Examiner* — Boniface N Nganga
(74) *Attorney, Agent, or Firm* — Scully, Scott, Murphy & Presser, PC

(57) ABSTRACT

A medical manipulator having: a longitudinal member; an arm body portion; a first bending portion; a second bending portion; an angle wire; a connecting rod; an operating wire; an arm operating portion including a guide member; wherein the arm operating portion has: a link portion; turning member; and an operating lever; wherein the turning member has: a rotating shaft which is slidably supported by the guide member so as to rotate around a coupling portion; and a guided member which is slidably engaged by the guide member so as to rotate around the rotating shaft in accordance with an operation of the operating lever.

6 Claims, 26 Drawing Sheets

Related U.S. Application Data continuation of application No. PCT/JP2010/067582, filed on Oct. 6, 2010.

(60) Provisional application No. 61/285,217, filed on Dec. 10, 2009.

(51) Int. Cl.
*A61B 17/29* (2006.01)
*A61B 34/00* (2016.01)
*A61B 17/00* (2006.01)
*A61B 17/34* (2006.01)
*A61B 34/30* (2016.01)

(52) U.S. Cl.
CPC .... *A61B 34/70* (2016.02); *A61B 2017/00318* (2013.01); *A61B 2017/00323* (2013.01); *A61B 2017/00353* (2013.01); *A61B 2017/2905* (2013.01); *A61B 2017/2906* (2013.01); *A61B 2017/2908* (2013.01); *A61B 2017/3445* (2013.01); *A61B 2017/3447* (2013.01); *A61B 2034/306* (2016.02)

(58) Field of Classification Search
CPC  A61B 2017/00323; A61B 2017/00353; A61B 2017/2905; A61B 2017/2906; A61B 2017/2908; A61B 2017/3445; A61B 2017/3447; A61B 2019/2238
USPC .............. 606/1, 106, 138–139; 600/146–152
See application file for complete search history.

(56) References Cited

U.S. PATENT DOCUMENTS

| | | | |
|---|---|---|---|
| 7,147,650 | B2 | 12/2006 | Lee |
| 7,364,582 | B2 | 4/2008 | Lee |
| 7,615,067 | B2 | 11/2009 | Lee et al. |
| 7,686,826 | B2 | 3/2010 | Lee et al. |
| 7,862,580 | B2 | 1/2011 | Cooper et al. |
| 7,930,065 | B2 | 4/2011 | Larkin et al. |
| 8,105,350 | B2 | 1/2012 | Lee et al. |
| 2002/0019591 | A1 | 2/2002 | Bon |
| 2004/0138525 | A1 | 7/2004 | Saadat et al. |
| 2005/0033357 | A1 | 2/2005 | Braun |
| 2005/0272977 | A1* | 12/2005 | Saadat ................. A61B 1/0008 600/114 |
| 2006/0155262 | A1 | 7/2006 | Kishi et al. |
| 2006/0229666 | A1 | 10/2006 | Suzuki et al. |
| 2007/0156019 | A1 | 7/2007 | Larkin et al. |
| 2007/0219581 | A1 | 9/2007 | Dohi et al. |
| 2007/0221700 | A1 | 9/2007 | Ortiz et al. |
| 2007/0249897 | A1 | 10/2007 | Miyamoto et al. |
| 2008/0065105 | A1* | 3/2008 | Larkin ............... A61B 1/00087 606/130 |
| 2008/0071289 | A1 | 3/2008 | Cooper et al. |
| 2008/0071291 | A1 | 3/2008 | Duval et al. |
| 2008/0221592 | A1 | 9/2008 | Kawai |
| 2008/0255423 | A1 | 10/2008 | Kondo et al. |
| 2008/0269557 | A1* | 10/2008 | Marescaux ............ A61B 1/018 600/106 |
| 2009/0105726 | A1 | 4/2009 | Sugiyama |
| 2009/0192521 | A1 | 7/2009 | Braun |
| 2009/0216077 | A1 | 8/2009 | Banju |
| 2010/0016666 | A1 | 1/2010 | Hasegawa |
| 2010/0154578 | A1 | 6/2010 | Duval |
| 2010/0331856 | A1* | 12/2010 | Carlson ............ A61B 1/00147 606/130 |
| 2011/0087269 | A1* | 4/2011 | Stokes .................. A61B 17/29 606/206 |
| 2011/0230894 | A1* | 9/2011 | Simaan ............. A61B 1/00183 606/130 |

FOREIGN PATENT DOCUMENTS

| | | |
|---|---|---|
| JP | 2008-93271 A | 4/2008 |
| JP | 2010-057914 A | 3/2010 |
| WO | 2008/099881 A1 | 8/2008 |

OTHER PUBLICATIONS

Japanese Office Action dated Jul. 19, 2011 from corresponding Japanese Patent Application No. JP 2011-516594 together with partial English language translation.

* cited by examiner

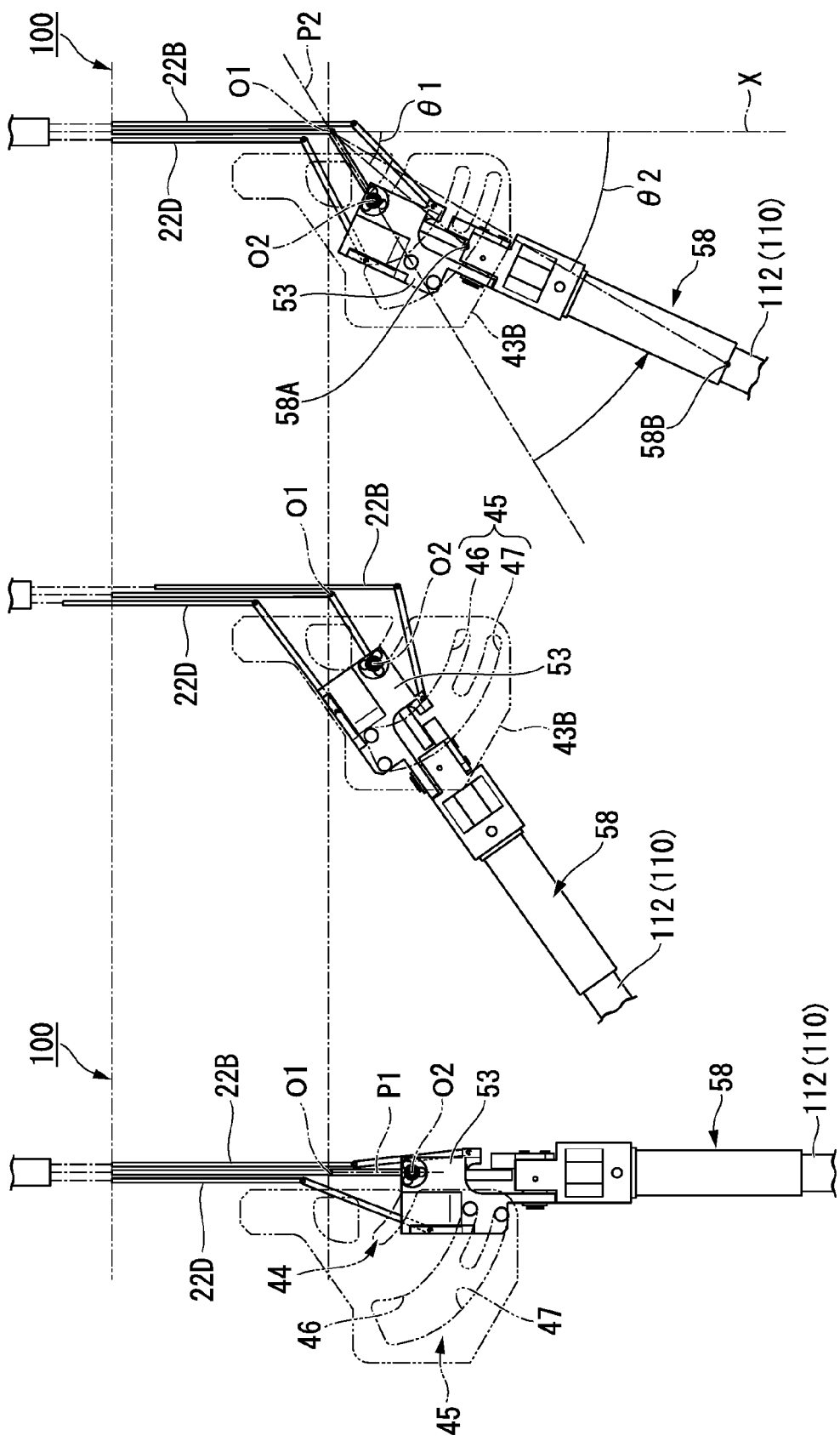

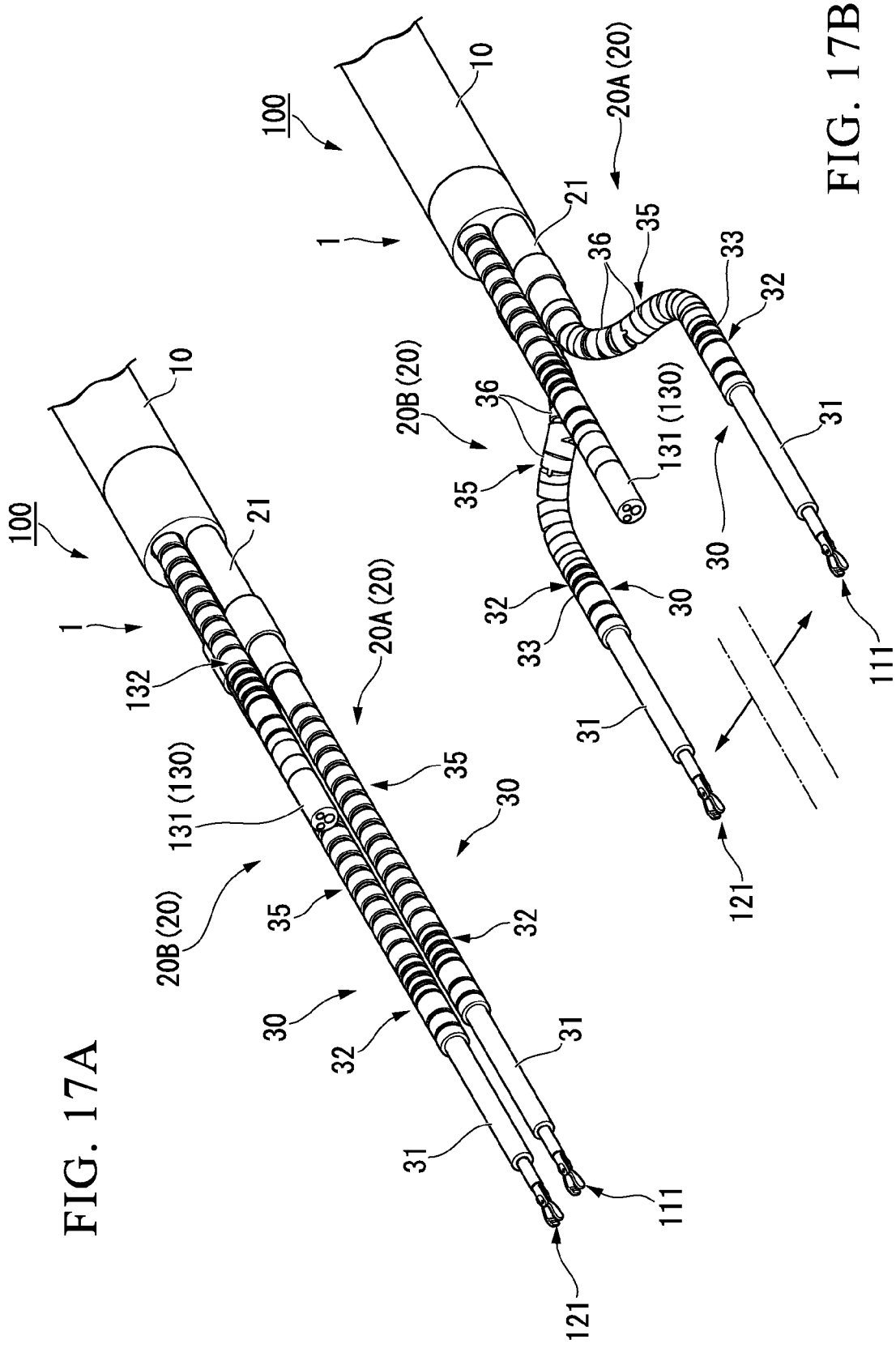

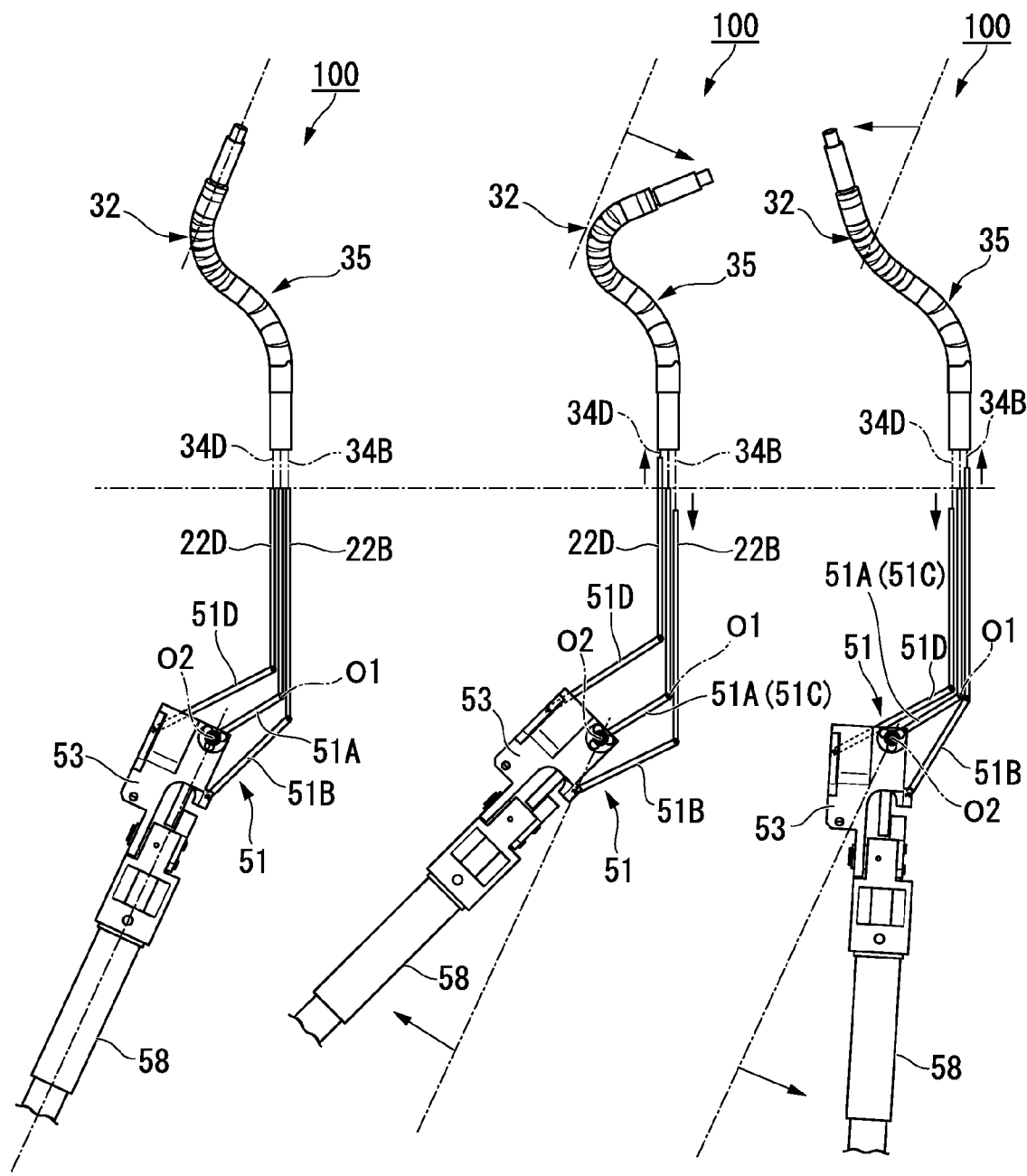

MEDICAL MANIPULATOR

CROSS-REFERENCE TO RELATED APPLICATIONS

This application is a continuation application of U.S. patent application Ser. No. 13/155,793, filed on Jun. 8, 2011, which is a continuation application of a PCT Patent Application No. PCT/JP2010/067582, filed on Oct. 6, 2010, whose priority is claimed on U.S. Provisional Application No. 61/285,217, filed on Dec. 10, 2009. The contents of these applications are entirely incorporated herein by reference.

BACKGROUND OF THE INVENTION

Field of the Invention

The present invention relates to a medical manipulator which is inserted into a body cavity, and is used when treatment is performed on various tissues in the body cavity.

Description of the Related Art

Conventionally, as an example of low invasive treatment, various procedures such as gallbladder extraction using a laparoscope or the like are performed. This kind of laparoscope procedure is performed by making a plurality of openings in the abdominal wall and a plurality of instruments being inserted therein.

In recent years, in order to reduce the burden on the patent by further reducing the number of openings to be made in the abdominal wall, it has been proposed to perform procedures by inserting a flexible endoscope from the patient's natural orifice such as the mouth, nose, or anus. As a medical device that is used in such a procedure, for example a treatment endoscope has been proposed as disclosed in U.S. Patent Application Publication No. 2007/0249897.

This treatment endoscope has a flexible insertion portion that has flexibility, and a pair of arm portions that have a bending portion that performs a bending action are provided at a distal end of the insertion portion, and a plurality of channels that are disposed in the insertion portion and lumens of the arm portions are continuous. The operating portion of the treatment endoscope is connected to the arm portions by an operating member, and is constituted to be capable of bendably operating the arm portions up/down or left/right.

The user inserts a treatment instrument such as forceps into the channel, mounts an operating portion of the treatment instrument to an operating portion of the treatment endoscope to project the distal end of the treatment instrument from the arm portion and operate the operating portion up/down or left/right, whereby a procedure is performed by causing the distal end of the treatment instrument to approach the tissue of the procedure target from a different direction.

SUMMARY OF THE INVENTION

According to an aspect of the present invention, a medical manipulator comprises: a longitudinal member which extends in a longitudinal axis direction; an arm body portion provided at a distal end of the longitudinal member; a first bending portion disposed at a distal end portion of the arm body portion; a second bending portion disposed at the distal end portion of the arm body portion and disposed at a more proximal side than the first bending portion; an angle wire which has a distal end part fixed to the first bending portion and has a proximal end part, the angle wire being movably inserted into the arm body portion; a connecting rod which is connected to the proximal end part of the angle wire, the connecting rod being movably inserted into the arm body portion; an operating wire fixed to the second bending portion and movably inserted into the arm body portion; and an arm operating portion including a guide member which is fixed to a proximal end part of the arm body portion, wherein the arm operating portion has: a link portion having a first end part of the link portion which is rotatably connected to a proximal end part of the connecting rod; a turning member rotatably connected to a second end part of the link portion; and an operating lever connected to the turning member, wherein the turning member has: a rotating shaft which is slidably supported by the guide member so as to rotate around a coupling portion in accordance with an operation of the operating lever, the coupling portion at which the connecting rod and the link portion are connected; and a guided member which is slidably engaged by the guide member so as to rotate around the rotating shaft in accordance with an operation of the operating lever, wherein the connecting rod is configured such that a position of the connecting rod in the longitudinal axis direction is fixed while the turning member rotates around the coupling portion and the turning member rotates around the rotating shaft in a direction opposite to a rotation direction which the turning member rotates around the coupling portion by operating the operating lever, wherein the operating wire is configured to be pulled to the arm operating portion side by which the turning member rotates around the coupling portion and rotates around the rotating shaft in a direction opposite to the direction in which the turning member rotates around the coupling portion by operating the operating lever, and wherein the second bending portion is bent by being pulled by the operation wire to the arm operating portion side.

BRIEF DESCRIPTION OF THE DRAWINGS

FIG. 16A, FIG. 16B, and FIG. 16C are action explanation drawings for explaining the action during use of the same treatment system.

FIG. 17A and FIG. 17B are action explanation drawings for explaining the action of the distal end portion during use of the same treatment system.

FIG. 19A, FIG. 19B, and FIG. 19C are action explanation drawings for explaining the action during use of the same treatment system.

DETAILED DESCRIPTION OF THE INVENTION

A treatment system 100 including a medical manipulator 1 (hereinafter simply referred to as a "manipulator") of one embodiment of the present invention will be described below. First, the configuration of the treatment system 100 and manipulator 1 will be described with reference to FIGS. 1 to 11B.

Figure 1:
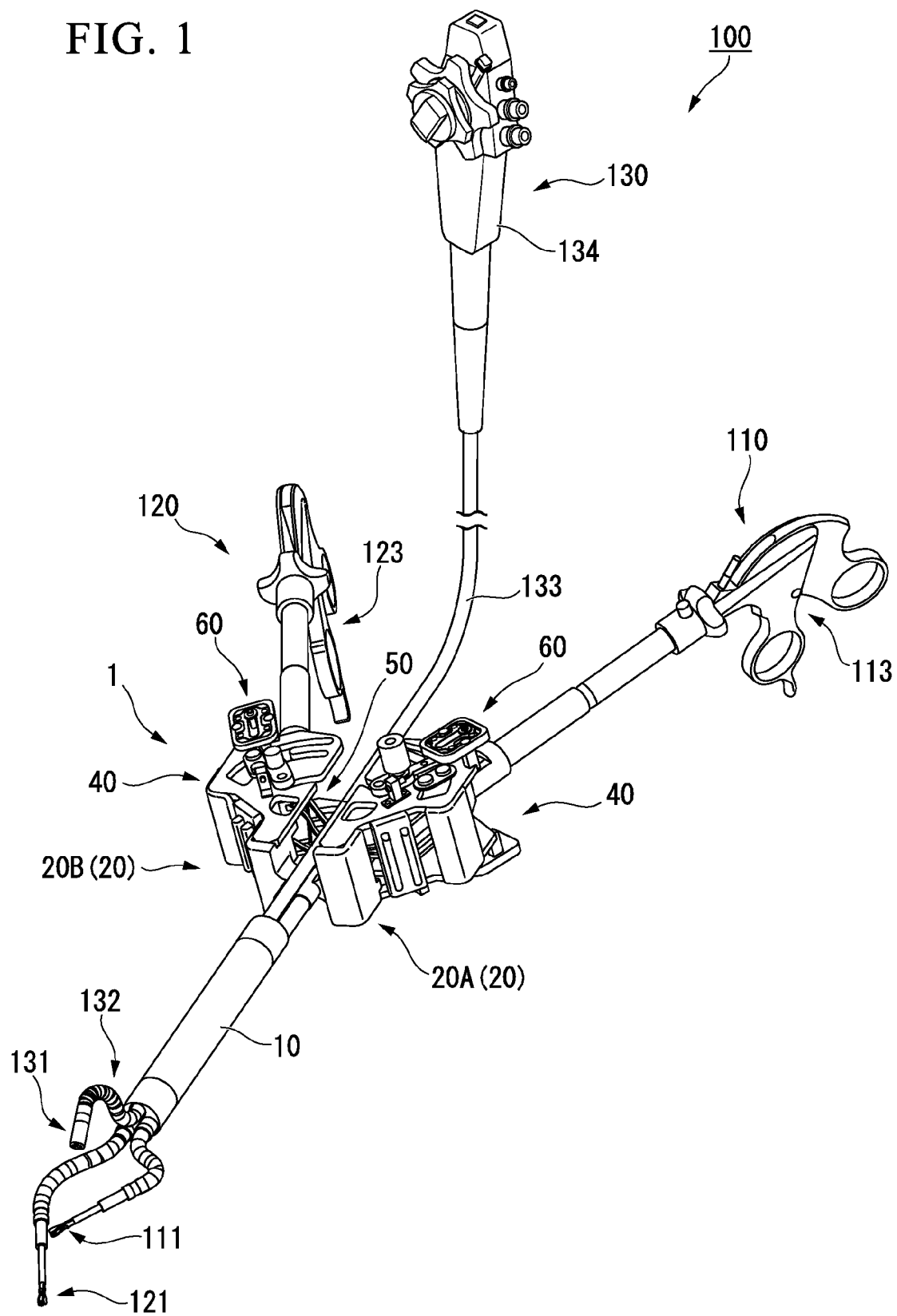
FIG. 1 is a perspective view that shows a treatment system that is provided with the medical manipulator of one embodiment of the present invention.
Figure 2:
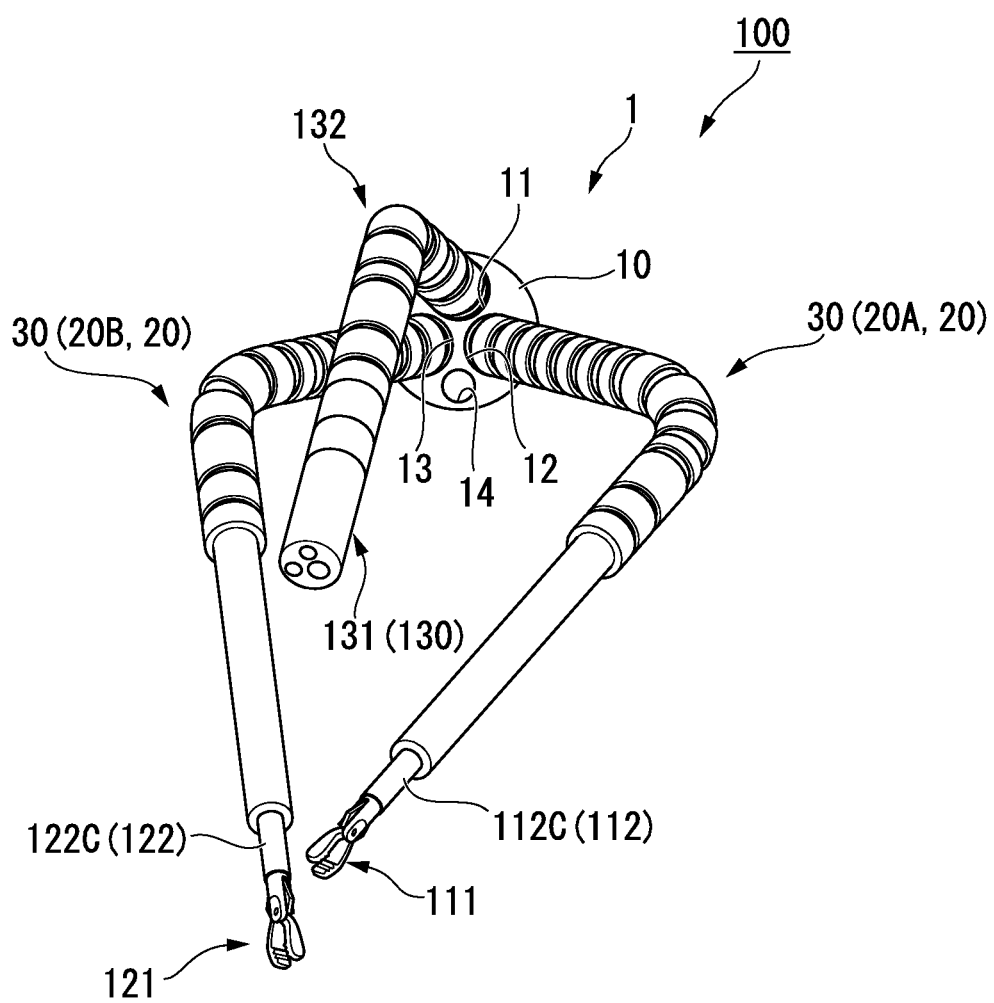
FIG. 2 is a front elevation view that shows the same treatment system.
Figure 3:
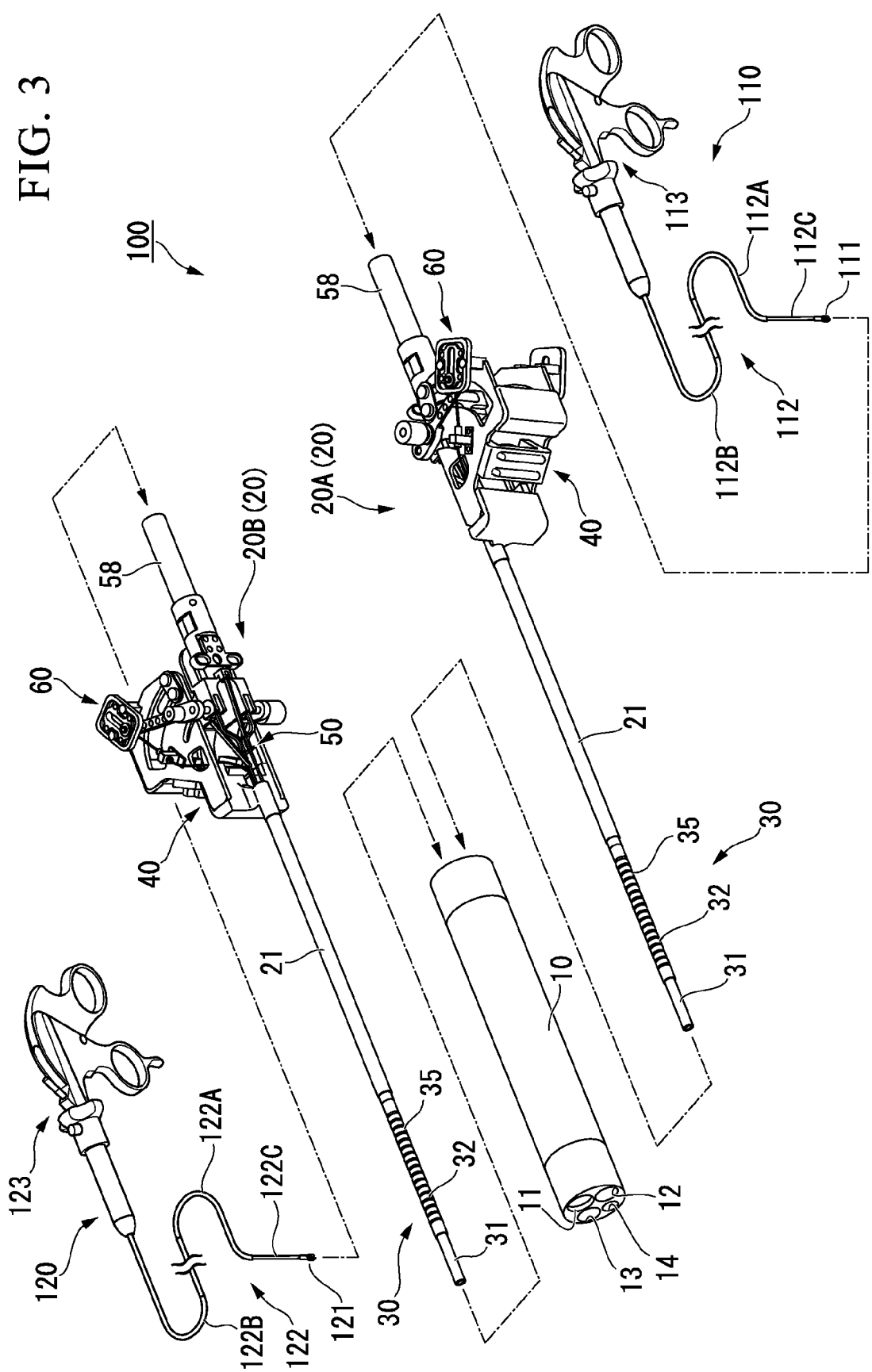
FIG. 3 is an exploded perspective view that shows the same treatment system.

FIG. 1 is an overall view showing the treatment system 100 including the manipulator 1 of the present embodiment. Additionally, FIG. 2 is a front view showing the treatment system 100. Additionally, FIG. 3 is an exploded perspective view showing the treatment system 100.

As shown in FIG. 1, the treatment system 100 includes a treatment tool 110, a treatment tool 120, an endoscope 130, and the manipulator 1.

As shown in FIGS. 1 and 2, the treatment tool 110 has a treatment portion 111 which performs a treatment within a body cavity, a long insertion portion 112 which has the treatment portion 111 fixed to one end thereof, and an operating portion 113 provided at the other end of the insertion portion 112 to operate the treatment portion 111.

As the treatment portion 111, an appropriate component, such as forceps or an incision implement can be adopted according to manipulation.

As shown in FIG. 3, the insertion portion 112 has flexible portions 112A and 112B at an intermediate portion thereof. The flexible portion 112A is a portion arranged at the position of a first bending portion 32 and a second bending portion 35 (which will be described below) when the treatment tool 110 is attached to the manipulator 1, and the flexible portion 112B is a portion arranged at the position of an arm operating portion 40 (which will be described below) when the treatment tool 110 is attached to the manipulator 1.

The treatment tool 120 has a treatment portion 121, an insertion portion 122, and an operating portion 123, similarly to the treatment tool 110.

As shown in FIG. 2, a treatment tool to be used after being inserted into the manipulator 1 is configured such that the distal sides of the insertion portion 112 and the insertion portion 122 have hard portions 112C and 122C formed from hard members or the like with a predetermined length. The hard portions 112C and 122C are formed with a length equivalent to the amount of advancing and retracting by which the treatment tools 110 and 120 advance and retract inside the manipulator 1, when the treatment tools 110 and 120 are attached to the manipulator 1 and the treatment tools 110 and 120 are used. This is to make a large force act on an object tissue, thereby performing manipulation, when the treatment portions 111 and 121 are made to project from the manipulator 1.

Additionally, when the portion (for example, the portion located at an arm body portion 21 which will be described below) which is not made to perform bending operation when the treatment tools 110 and 120 are attached to the manipulator 1 is formed from a hard member similarly to the hard portions 112C and 122C, since the force applied to the treatment portions 111 and 121 from the operating portions 113 and 123 can be efficiently transmitted in order to operate the treatment portions 111 and 121, this is preferable.

As shown in FIGS. 1 and 2, a well-known endoscope can be appropriately adopted as the endoscope 130. For example, the endoscope 130 includes an imaging portion 131 which images the inside of a body cavity, a bending portion 132 which is capable of performing a bending operation and has the imaging portion 131 fixed to one end thereof, an insertion portion 133 which is connected to the bending portion 132 and guides the imaging portion 131 into the body cavity, and an operating portion 134 which operates the imaging portion 131 and the bending portion 132 through the inside of the insertion portion 133. In the present embodiment, in the bending portion 132 of the endoscope 130, two bending piece portions (not shown) which perform bending operation mutually independently are provided in a line in the longitudinal direction of the bending portion 132 (or apart from each other in the longitudinal direction). The two bending piece portions have a plurality of joint rings, respectively, and the bending operation of the two bending piece portions can be performed independently or in cooperation with each other. When the bending operation of the two bending piece portions is performed in the bending portion 132, the imaging portion 131 can be moved parallel to the longitudinal axis of the insertion portion 133, or the imaging portion 131 can be directed to an object which becomes an object to be imaged after the imaging portion 131 is moved in parallel in this way. Thereby, an excellent visual field in which the point of view of the imaging portion 131 is directed to the region of interest in an object can be obtained. In addition, the bending piece portions provided at the bending portion 132 may be more than two. Additionally, in a case where the bending portion 132 has one bending piece portion, the above-described parallel movement cannot be performed. However, if the position of the manipulator 1 in a body cavity is suitable, the imaging portion 131 can be directed to an object even if only one bending piece portion is provided.

The configuration of the manipulator 1 of the present embodiment will be described below.

As shown in FIGS. 1 to 3, the manipulator 1 includes the insertion portion 10 inserted into a body cavity, and the arm portion 20 used after being inserted into the insertion portion 10.

The insertion portion 10 is formed substantially in the shape of a tube having four channels (a channel 11, a channel 12, a channel 13, and a channel 14, which may be referred to as "channels 11 to 14" below).

The channel 11 is a through-hole for allowing the insertion portion 133 of the above-described endoscope 130 to be inserted therethrough.

The channel 12 and the channel 13 are through-holes with a round cross-sectional shape within a plane orthogonal to the longitudinal direction of the insertion portion 10. The internal diameters of the channel 12 and the channel 13 are equal to each other, a first arm 20A which will be described below is inserted through the channel 12, and a second arm 20B which will be described below is inserted through the channel 13. In addition, the second arm 20B can be inserted through the channel 12, and the first arm 20A can also be inserted through the channel 13.

The relative positions of the first arm 20A and the second arm 20B are defined by the channel 12 and the channel 13. In the present embodiment, the channel 12 and the channel 13 are arranged at positions equidistant from the channel 11, and the first arm 20A and the second arm 20B inserted through the channel 12 and the channel 13 are positioned at positions equidistant from the channel 11.

In addition, in the insertion portion 10, the positions of channels 12 and 13 can be independently determined. For example, in order to bring the position of the treatment portions 111 and 121 in the treatment tools 110 and 120 into the optimal positional relationship for every manipulation using the manipulator 1, the channels 12 and 13 can also be formed in the insertion portion 10 with the positional relationship between the channels 12 and 13 being an appropriate positional relationship. Specifically, the insertion portion 10 may be formed such that the positions of openings of the channels 12 and 13 on the distal side or the positions of openings of the channels 12 and 13 on the proximal side are made different in the longitudinal direction of the insertion portion 10 between the channel 12 and the channel 13. In this case, when the first arm 20A and the second arm 20B are attached to the channels 12 and 13, the positions of the respective tips of the first arm 20A and the second arm 20B are different in a longitudinal axis direction of the insertion portion 10, and the positions of the treatment portions 111 and 121 of the treatment tools 110 and 120 inserted through the first arm 20A and the second arm 20B, respectively, are also different in the longitudinal axis direction of the insertion portion 10. Thereby, the treatment tools 110 and 120 can be guided such that the positions of the treatment portions 111 and 121 become appropriate positions with respect to an object to be treated.

In addition, the channels 12 and 13 can be provided at appropriate positions within the insertion portion 10 according to manipulation, and the relative position relationship between the channel 12 and the channel 13 with respect to the channel 11 and the channel 14 can be brought into an appropriate positional relationship within the insertion portion 10.

The channel 14 is a through-hole for allowing an appropriate treatment tool (not shown) or the like to be inserted therethrough, or for performing air supply, water supply, or suction.

As shown in FIG. 3, the arm portion 20 includes the first arm 20A to be used while allowing the treatment tool 110 to be inserted therethrough, and the second arm 20B to be used while allowing the treatment tool 120 to be inserted therethrough. The first arm 20A and the second arm 20B of the present embodiment are configured with the same shape and size.

In addition, in order to band the first arm 20A and the second arm 20B together in a state where the first arm 20A and the second arm 20B are attached to the insertion portion 10, for example, a band formed from resin or the like may be attached to the first arm 20A and the second arm 20B on the distal side of the insertion portion 10. Additionally, the treatment tool 120 may be attached to the first arm 20A, and the treatment tool 110 may be attached to the second arm 20B. In the following, a case where the treatment tool 110 is attached to the first arm 20A and the treatment tool 120 is attached to the second arm 20B will be described.

Additionally, in the following, the configuration of the first arm 20A will be described, and description of duplicate portions in the configuration of the second arm 20B will be omitted.

Figure 4A:
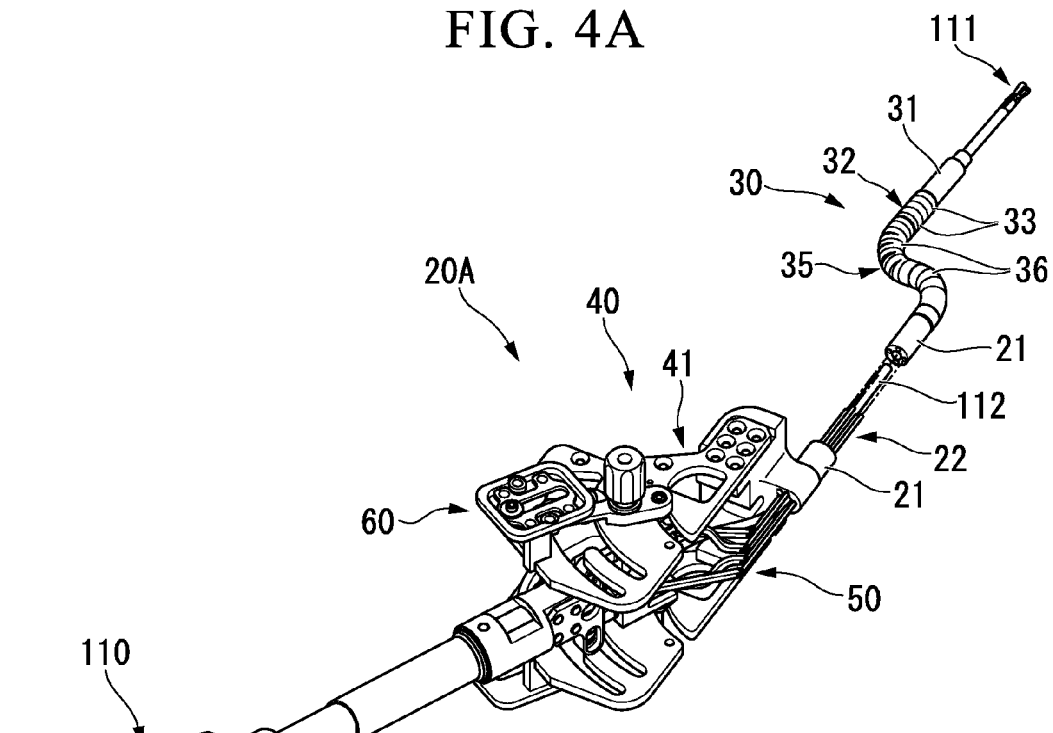
FIG. 4A and FIG. 4B are perspective views that show partial constitutions of the same treatment system.
Figure 4B:
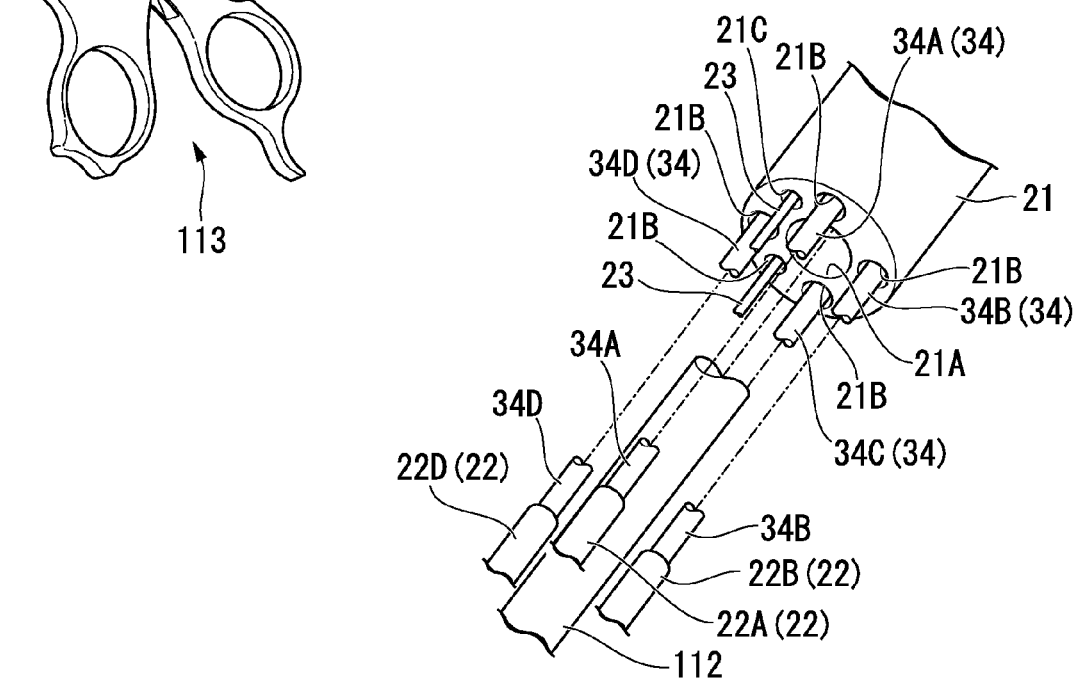

FIGS. 4A and 4B are perspective views showing the configuration of the first arm 20A. In addition, in order to make the configuration of the first arm 20A easily understood, illustration of some of the configuration is omitted in FIGS. 4A and 4B.

As shown in FIG. 4A, the first arm 20A includes the arm body portion 21 which is formed in a tubular shape, an arm tip portion 30 provided at the tip of the arm body portion 21, and the arm operating portion 40 provided at the proximal end of the arm body portion 21.

As shown in FIG. 4B, the arm body portion 21 is formed such that a treatment tool lumen 21A for allowing the treatment tool 110 to be inserted therethrough passes through the central portion of the arm body portion 21 and extends in the longitudinal direction. Moreover, four transmission member insertion hole portions 21B and two second operating wire insertion hole portions 21C, which pass through the arm body portion 21 and extend in the longitudinal direction, are formed radially outside the treatment tool lumen 21A in the arm body portion 21.

The treatment tool lumen 21A is a through-hole in which the treatment portion 111 and the insertion portion 112 of the treatment tool 110 can advance and retract freely, and the cross-sectional shape thereof within a plane orthogonal to thelongitudinal direction of the arm body portion 21 become a round shape.

A transmission member 22 for transmitting the operation input in the arm operating portion 40 to the first bending portion 32 (which will be described below) of the arm tip portion 30 is provided inside the transmission member insertion hole portion 21B.

The transmission member 22 has rod-shaped connecting rods (a connecting rod 22A, a connecting rod 22B, a connecting rod 22C, and a connecting rod 22D, which may be referred to as "connecting rods 22A to 22D" below), and the connecting rods 22A to 22D are inserted through the four transmission member insertion hole portions 21B, respectively, so as to advance and retract freely therein. In addition, since the connecting rod 22C is hidden inside the insertion portion 112 of the treatment tool 110, this connecting rod is not shown in FIGS. 4A and 4B.

A second operating wire 23 for transmitting the operation input in the arm operating portion 40 to the second bending portion 35 (which will be described below) of the arm tip portion 30 is provided inside the second operating wire insertion hole portion 21C.

Two second operating wires 23 are provided in the present embodiment. The two second operating wires 23 are inserted through the two second operating wire insertion hole portions 21C, respectively, so as to advance and retract freely. Additionally, the tips of the second operating wire 23 are fixed to the second bending portion 35 of the arm tip portion 30 which will be described below. Since the two second operating wires 23 are provided in the present embodiment, the amount of a pulling force applied to each second operating wire 23 can be reduced. For this reason, loss of the amount of a pulling force caused by the elongation of the second operating wire 23 when the second operating wire 23 is pulled, wobbling or the like of the second bending portion 35 which will be described below can be reduced.

The arm tip portion 30 has a tip hard portion 31 from which the treatment portion 111 of the treatment tool 110 is paid out, the first bending portion 32 provided on the proximal side of the tip hard portion 31, and the second bending portion 35 provided on the proximal side of the first bending portion 32.

The tip hard portion 31 is formed substantially in the shape of a tube which has a treatment portion lumen 31A through which the treatment portion 111 of the treatment tool 110 can be inserted. The tip hard portion 31 is adapted so as not to bend unlike the first bending portion 32 and the second bending portion 35.

A plurality of joint rings (a first joint ring 33 and a second joint ring 36) are coupled to the first bending portion 32 and the second bending portion 35 so as to align in the axis direction of the arm tip portion 30. In the present embodiment, as for the first joint ring 33 and the second joint ring 36, the first joint ring 33 is arranged relatively closer to the distal side, and the second joint ring 36 is arranged relatively closer to the proximal side. The shape of the first joint ring 33 and the second joint ring 36 become a ring shape, and the treatment portion 111 of the treatment tool 110 inserted through the first bending portion 32 and the second bending portion 35 is paid out from the tip hard portion 31 through the first joint ring 33 and the second joint ring 36.

Although not shown in detail, the tip of an angle wire portion (transmission member) 34 for performing a bending operation of the first bending portion 32 is fixed to the tip of the first joint ring 33 of the first bending portion 32. As shown in FIG. 4B, the angle wire portion 34 is composed of four angle wires (an angle wire 34A, an angle wire 34B, an angle wire 34C, and an angle wire 34D, which may be referred to as "angle wires 34A to 34D" below). The tips of the angle wires 34A to 34D are fixed to the tip of the first joint ring 33, respectively, so as to be separated from each other by 90 degrees in the circumferential direction. The proximal ends of the angle wires 34A to 34D are connected to the tips of connecting rods 22A to 22D, respectively.

In addition, the connection spots between the connecting rods 22A to 22D and the angle wires 34A to 34D are preferably located on the distal side of the arm body portion 21 on the side closer to the proximal side than the second bending portion 35. This is to make the force which bends the first bending portion 32 efficiently transmitted by the hard connecting rods 22A to 22D.

The arm operating portion 40 performs pulling operation of the transmission member 22 and the angle wire portion 34, or the second operating wire 23, thereby performing a bending operation of the first bending portion 32 or the second bending portion 35, respectively. The arm operating portion 40 has a first bending operating portion 50 for performing a bending operation of the first bending portion 32, a second bending operating portion 60 for performing a bending operation of the second bending portion 35, and an operating body 41 having the first bending operating portion 50 and the second bending operating portion 60 coupled thereto, and fixed to the proximal end of the arm body portion 21.

Figure 5:
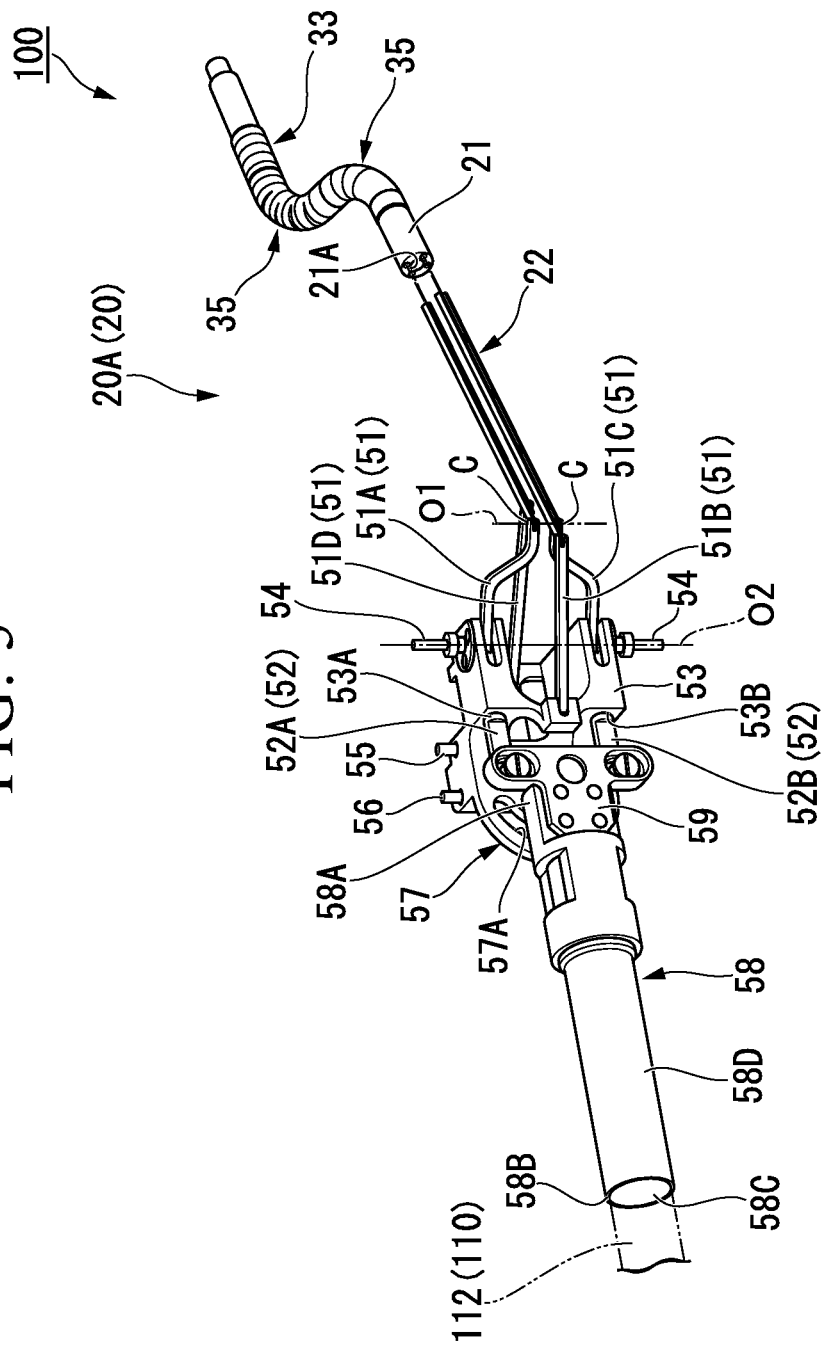
FIG. 5 is a perspective view that shows a partial constitution of the same treatment system.

FIG. 5 is a perspective view showing the configuration of a portion of the treatment system 100, and omitting illustration of some of the configuration in order to illustrate the first bending operating portion 50. Additionally, FIG. 6 is a plan view showing the first bending operating portion 50.

Figure 6:
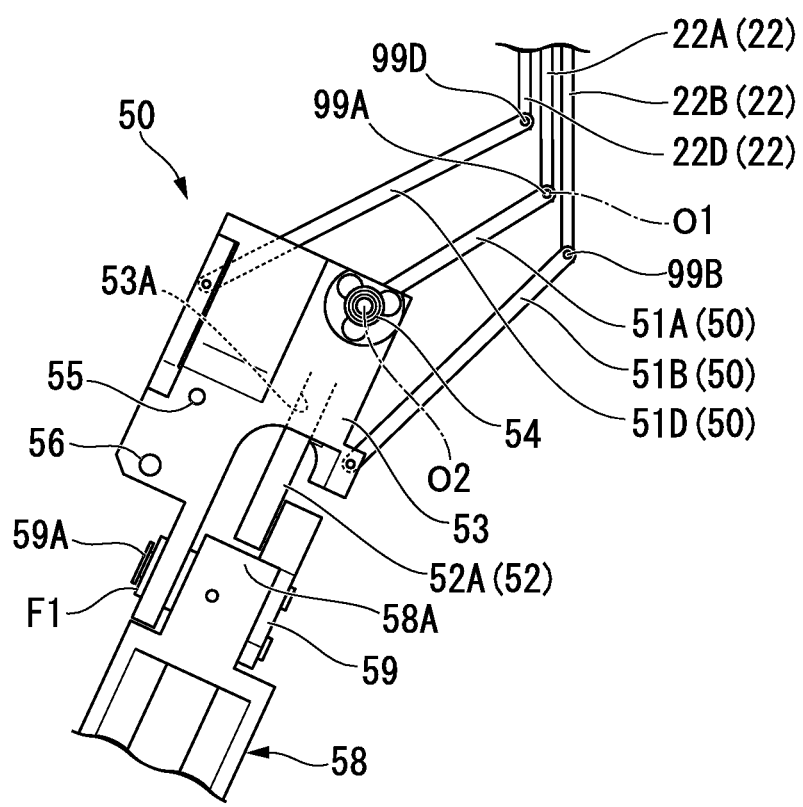
FIG. 6 is a plan view that shows a partial constitution of the same treatment system.

As shown in FIGS. 5 and 6, the first bending operating portion 50 has a link portion 51 having four links (a link 51A, a link 51B, and a link 51D) one end of each of which is coupled via a respective coupler (see, e.g., 99A, 99B, and 99D of FIG. 6) to the transmission member 22, a slider link portion 52 having the other ends of the link 51A and link 51C of the link portion 51 coupled thereto, and a turning member 53 having the slider link portion 52 supported thereon so as to advance and retract freely and having the other ends of the link 51B and link 51D of the link portion 51 coupled thereto, and a tubular operating lever 58 coupled to the turning member 53 and provided so as to extend toward the proximal side.

The slider link portion 52 has a first rod-shaped slider 52A and a second rod-shaped slider 52B, and the ends of the first slider 52A and the second slider 52B opposite to the side where the link 51A and the link 51C are coupled together are connected to a connecting portion 59 (which will be described below) of the operating lever 58.

The turning member 53 is formed with a through-hole 53A and a through-hole 53B through which the first rod-shaped slider 52A and second rod-shaped slider 52B of the slider link portion 52 can be inserted so as to advance and retract freely. Additionally, the turning member 53 has a turning shaft portion 54, a first guide pin 55, and a second guide pin 56 which are coupled to the operating body 41 which will be described below, and a vertical movement guide 57 which is formed to be a portion of an arc.

Two turning shaft portions 54 are formed so as to protrude mutually outward from the turning member 53. The central axis of the turning shaft portion 54 becomes a second turning center O2 for turning the turning member 53. Additionally, the second turning center O2 passes through a coupling portion between the link 51A and the link 51C, and the slider link portion 52 in a state where the first bending portion 32 is not bent.

The first guide pin 55 and the second guide pin 56 are formed so as to extend parallel to each other in the same direction as the direction in which the turning shaft portion 54 extends, and are formed so as to protrude from the external surface of the turning member 53.

The vertical movement guide 57 is formed with a through-hole 57A in which the turning member 53 is hollowed in the shape of an arc. The through-hole 57A is formed such that the center of the arc becomes the center of oscillation when the operating lever 58 is oscillated in a vertical direction.

The operating lever 58 is a tubular member in which a treatment tool insertion port 58C for allowing the insertion portion 112 of the treatment tool 110 to be inserted therethrough is formed, and has a connecting portion 59 coupled to the turning member 53, and a tubular grip portion 58D which extends toward the proximal side more than the turning member 53.

The distal side of the treatment tool insertion port 58C opens to the inside of the turning member 53, and the treatment tool 110 inserted through the treatment tool insertion port 58C is inserted into the treatment tool lumen 21A of the arm body portion 21 through a cavity portion inside the turning member 53.

Figure 7:
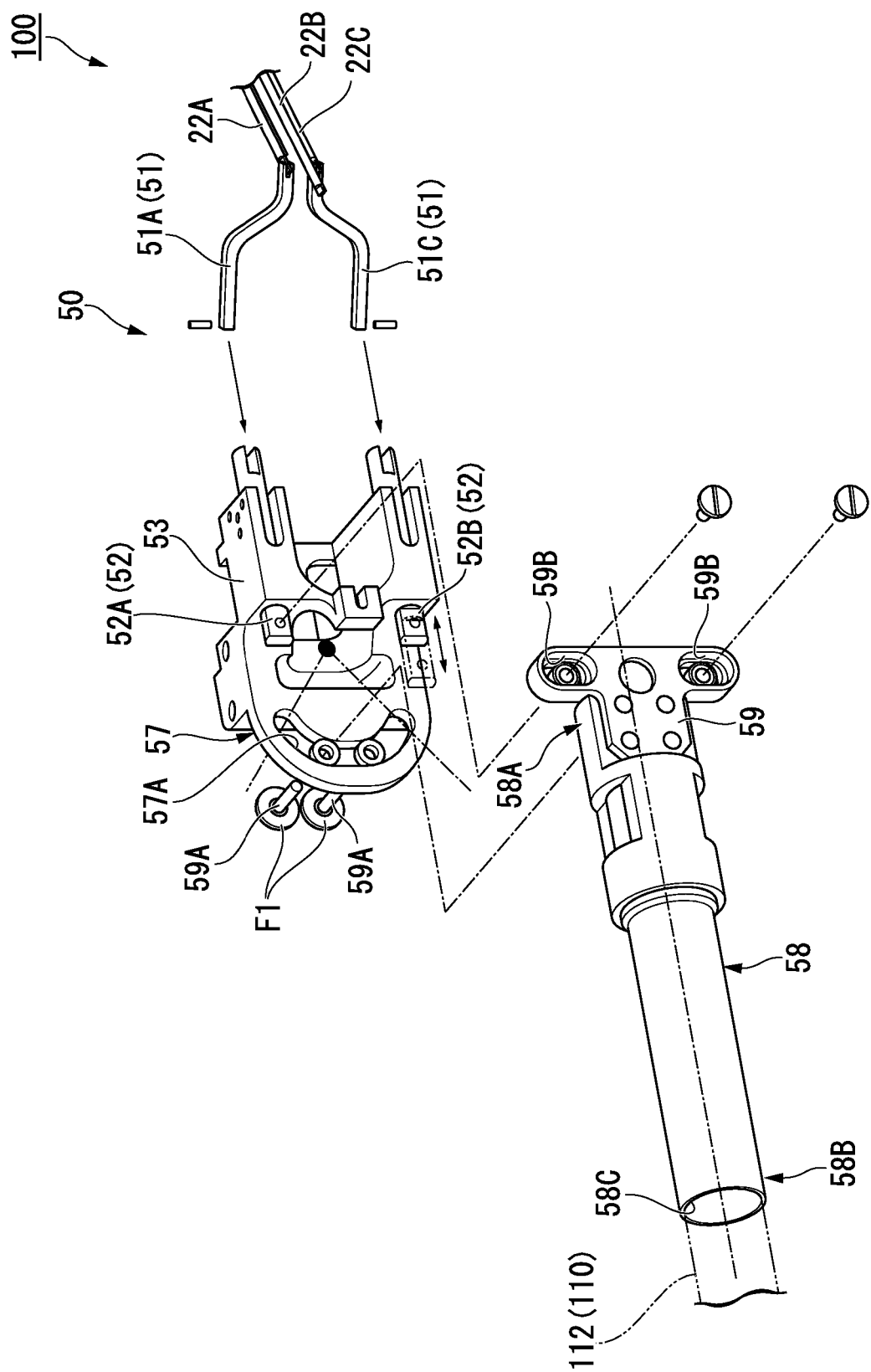
FIG. 7 is an exploded perspective view that shows a partial constitution of the same treatment system.

FIG. 7 is an exploded perspective view showing the configuration of a portion of the treatment system 100, and omitting illustration of some of the configuration in order to illustrate the first bending operating portion 50. As shown in FIG. 7, the connecting portion 59 has vertical movement guide pins 59A which touch the inner wall of the through-hole 57A, which is formed in the vertical movement guide 57 provided at the turning member 53, via a bearing, and sliding members F1 which are interposed between the vertical movement guide pins 59A and the vertical movement guide 57.

The sliding members F1 are provided at the vertical movement guide pins 59A, respectively, and can be formed from, for example, a material having elasticity.

Moreover, the connecting portion 59 is formed with slider coupling hole portions 59B for being coupled to the first slider 52A and second slider 52B of the slider link portion 52 via pins. Two slider coupling portions 59B are formed in the connecting portion 59, and the respective shapes thereof become a long hole shape.

Figure 8A:
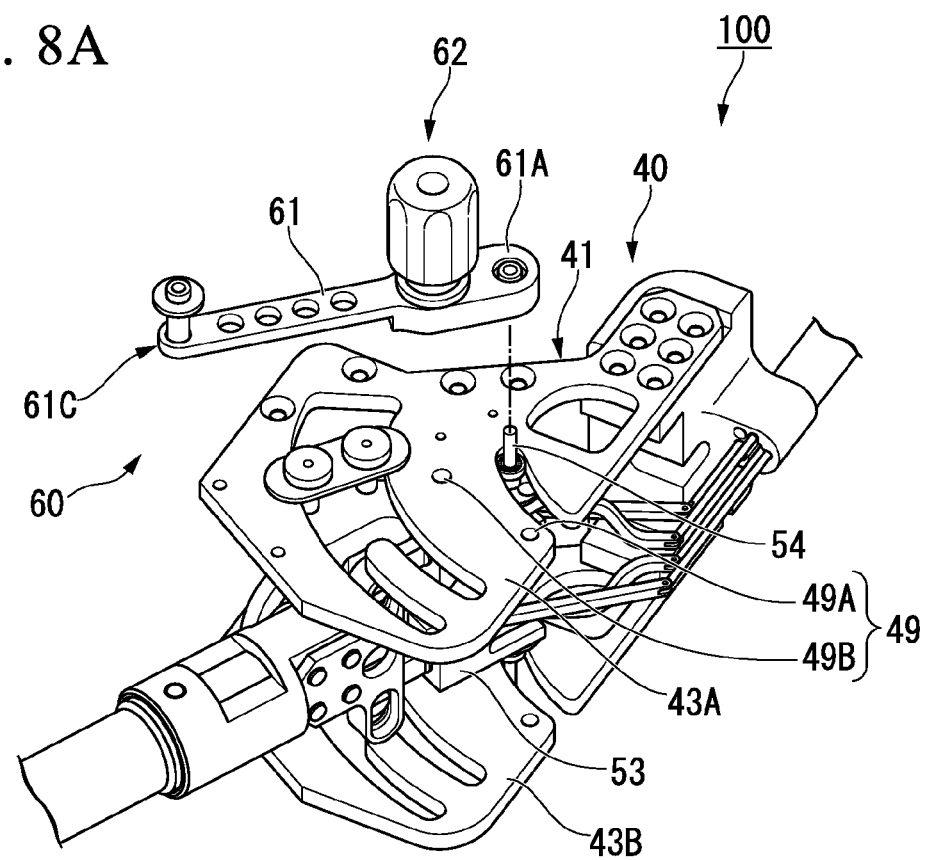
FIG. 8A is a perspective view that shows a partial constitution of the same treatment system.
Figure 8B:
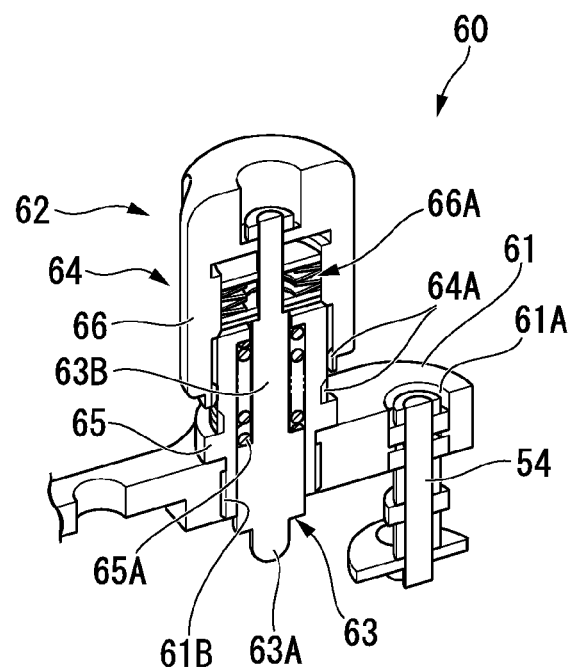
FIG. 8B is an enlarged cross-sectional view that shows a partial constitution of the same treatment system.

FIGS. 8A and 8B are perspective views showing the configuration of a portion of the treatment system 100, and omitting some of the configuration in order to illustrate the second bending operating portion 60. Additionally, FIGS. 9A and 9B are plan views showing the configuration of a portion of the treatment system 100, and omitting some of the configuration in order to illustrate the second bending operating portion 60.

As shown in FIGS. 8A to 9B, the second bending operating portion 60 has a coupling rod 61 whose one end 61A is turnably coupled to the turning shaft portion 54 of the turning member 53, a positioning portion 62 which couples together the coupling rod 61 and the operating body 41 and positions the coupling rod 61 with respect to the operating body 41, and a pulling guide portion 67 to which the other end 61C of the coupling rod 61 fits.

As shown in FIGS. 8A and 8B, the coupling rod 61 has a through-hole 61B, which is formed so as to extend in a direction facing a guide plate 43A (which will be described below) of the operating body 41, between one end 61A and the other end 61C. In addition, the through-hole formed between the through-hole 61B and the other end 61C is a lightened portion for reducing the weight of the coupling rod 61.

Figure 9A:
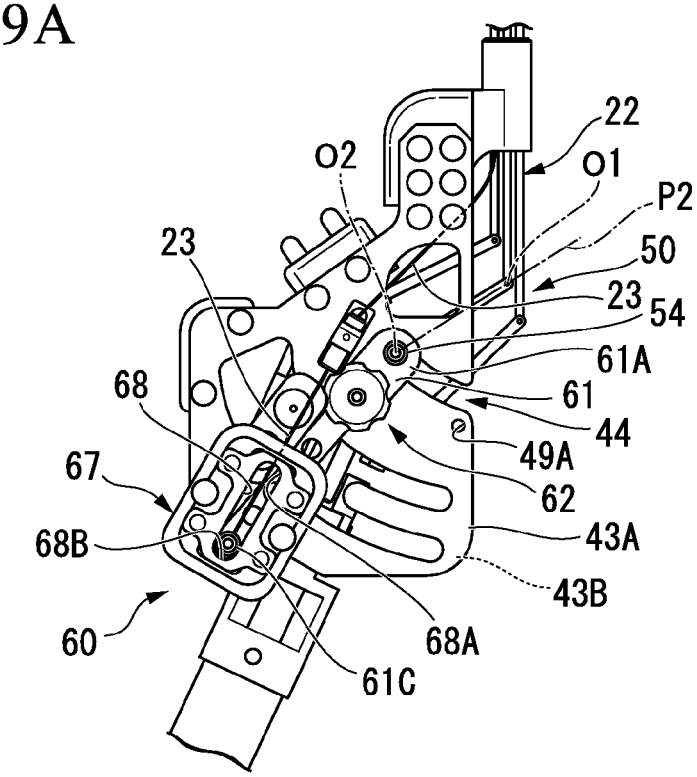
FIG. 9A and FIG. 9B are plan views that show a partial constitution of the same treatment system.
Figure 9B:
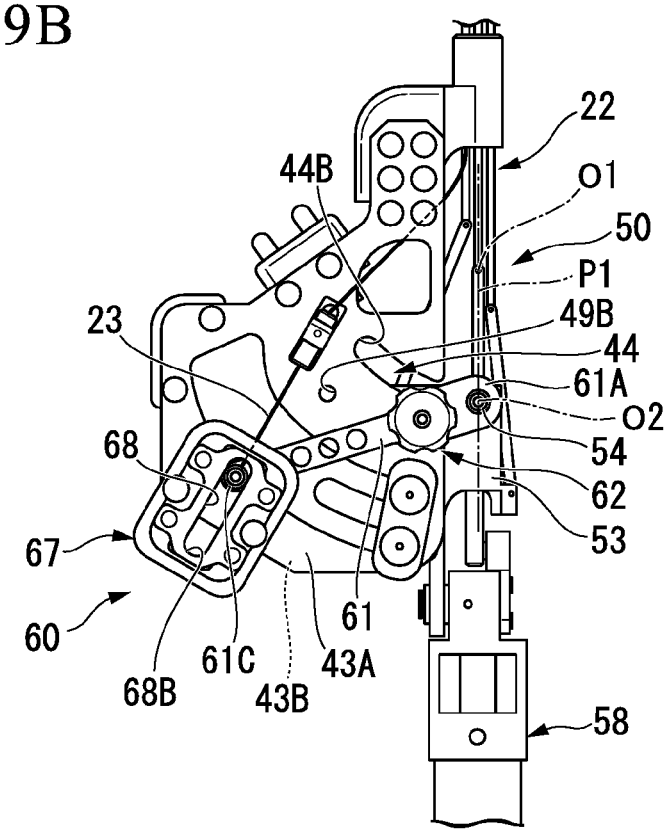

As shown in FIG. 9A, the proximal end of the second operating wire 23 is fixed to the other end 61C of the coupling rod 61.

As shown in FIGS. 8A and 8B, the positioning portion 62 has a positioning pin 63 which engages a dent 49A and a through-hole 49B which are formed in the guide plate 43A (which will be described below) of the operating body 41, and a pin lever 64 which supports the positioning pin 63 and is formed with a larger diameter than the positioning pin 63.

The positioning pin 63 is formed with a tip engaging portion 63A of which the tip has a semispherical shape, and a shaft portion 63B which extends through the through-hole 61B and is fixed to the pin lever 64.

The pin lever 64 has a substantially tubular fixed portion 65 which is inserted into and fixed to the through-hole 61B of the coupling rod 61, a coiled spring 65A which biases the positioning pin 63 toward the operating body 41 inside the fixed portion 65, a pin operating portion 66 which fits to the outer peripheral surface of the fixed portion 65 and is fixed to the shaft portion 63B of the positioning pin 63, and a disc spring portion 66A which is provided inside the pin operating portion 66.

Additionally, the pin lever 64 and the fixed portion 65 are formed with a set of threaded portions 64A for adjusting a biasing force which biases the positioning pin 63 toward the operating body 41 by the disc spring portion 66A. The threaded portions 64A can make it hard for the positioning pin 63 to slip off the through-hole 49B by rotating the pin operating portion 66 around an axis with respect to the fixed portion 65.

As shown in FIGS. 9A and 9B, the pulling guide portion 67 has a through-hole 68 which becomes a cam which converts the operating direction of the coupling rod 61 into the pulling direction of the second operating wire 23. The through-hole 68 becomes a long hole long in a direction in which the proximal end of the second operating wire 23 extends, and the other end 61C of the coupling rod 61 is adapted to be able to reciprocate between the one end 68A and other end 68B of the through-hole 68.

Additionally, the other end 61C of the coupling rod 61 is located at the other end 68B of the through-hole 68 of the pulling guide portion 67 in a state where the positioning pin 63 is inserted into the through-hole 49B by the above-described positioning portion 62. At this time, the direction in which the proximal end of the second operating wire 23 extends and the longitudinal axis direction of the coupling rod 61 substantially coincide with each other. In this positional relationship, the second operating wire 23 can be constrained within a range of the strength of the coupling rod such that the pulling state of the second operating wire 23 is held by a so-called toggle mechanism (boosting mechanism). As the above-described toggle mechanism is adopted in the second bending operating portion 60, when the second operating wire 23 is pulled in order to perform bending operation of the second bending portion 35, a sufficient amount of pulling force can be applied to the second operating wire 23 with a light force.

Figure 10A:
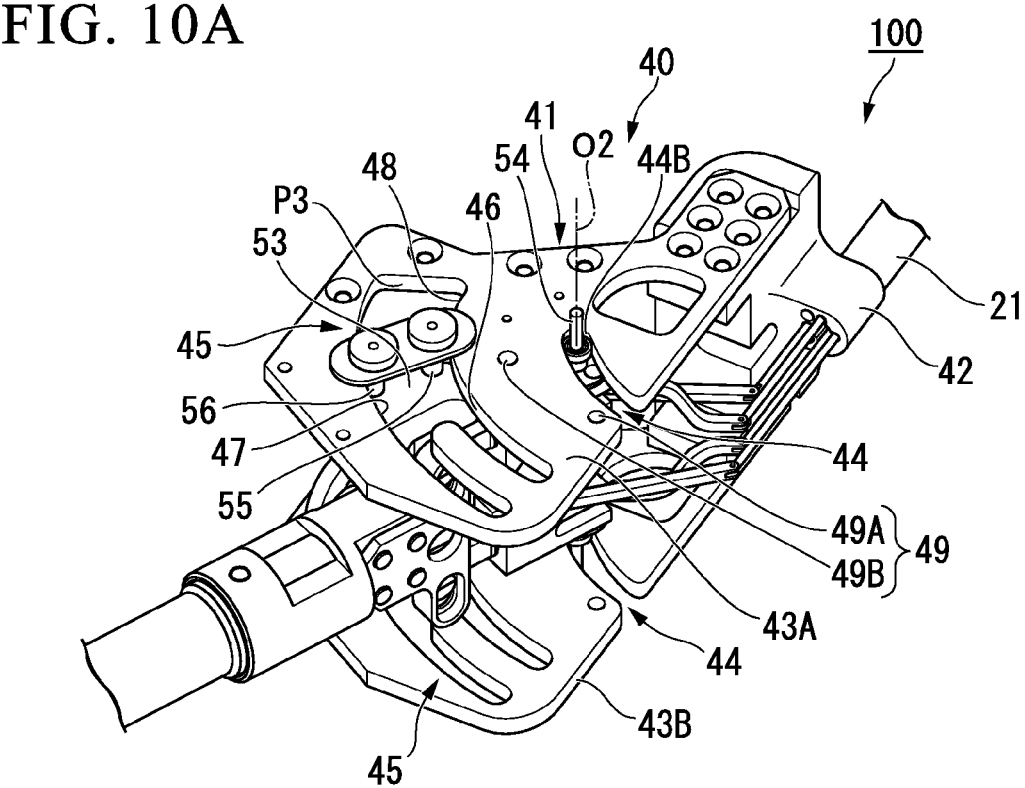
FIG. 10A and FIG. 10B are perspective views that show a partial constitution of the same treatment system.
Figure 10B:
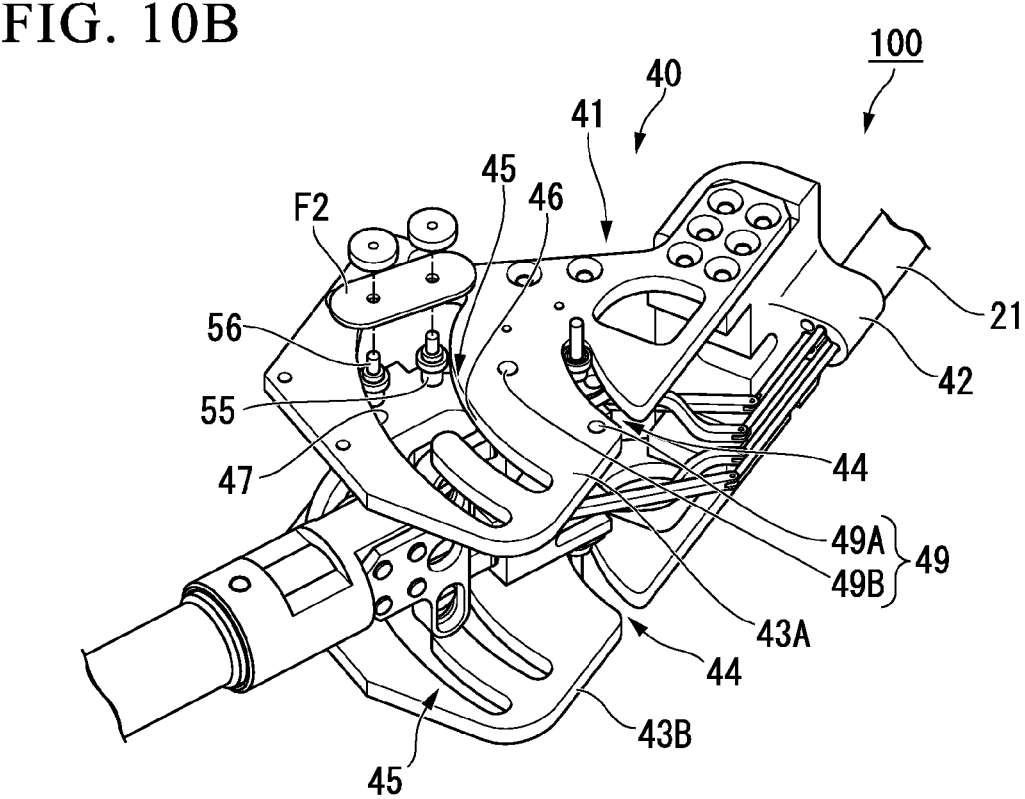

FIGS. 10A and 10B are perspective views showing the configuration of a portion of the treatment system 100, and omitting some of the configuration in order to illustrate the operating body 41.

The operating body 41 has a tip coupling portion 42 fixed to the arm body portion 21, and a substantially plate-shaped guide plate 43A and guide plate 43B fixed to the tip coupling portion 42.

The tip coupling portion 42 is formed with a through-hole which communicates with the treatment tool lumen 21A, the transmission member insertion hole portions 21B, and the second operating wire insertion hole portions 21C, which are formed in the arm body portion 21 (refer to FIG. 4B in regard to all of these).

The distal sides of the guide plate 43A and the guide plate 43B are fixed to the tip coupling portion 42, and the guide plate 43A and the guide plate 43B are arranged to face each other such that the planar directions thereof become parallel to each other. The guide plate 43A is formed with a first guide groove 44 and a second guide groove 45 which are hollowed through the guide plate 43A in the thickness direction of the guide plate 43A.

Moreover, the guide plate 43A is provided with a positioning hole portion 49 which engages with the positioning pin 63 of the positioning portion 62 provided on the second bending operating portion 60 shown in FIG. 8B. The positioning hole portion 49 is provided with the dent 49A formed on the guide plate 43A, and the through-hole 49B formed through the guide plate 43A in the thickness direction.

The shape of the dent 49A becomes a substantially semispherical shape to which the tip engaging portion 63A of the above-described positioning pin 63 (refer to FIG. 8B) fits. Additionally, the shape of the dent 49A preferably becomes such a shape that the engagement between the tip engaging portion 63A and the dent 49A is released when the positioning pin 63 is pressed toward a direction orthogonal to the thickness direction of the guide plate 43A. Specifically, it is preferable that the shape of an opening end which opens to the surface of the guide plate 43A incline with respect to the thickness direction of the guide plate 43A.

In addition, although not shown in detail, the guide plate 43B is formed in a shape symmetrical with respect to a plane with the planar direction of the guide plate 43A as a basis.

Figure 11A:
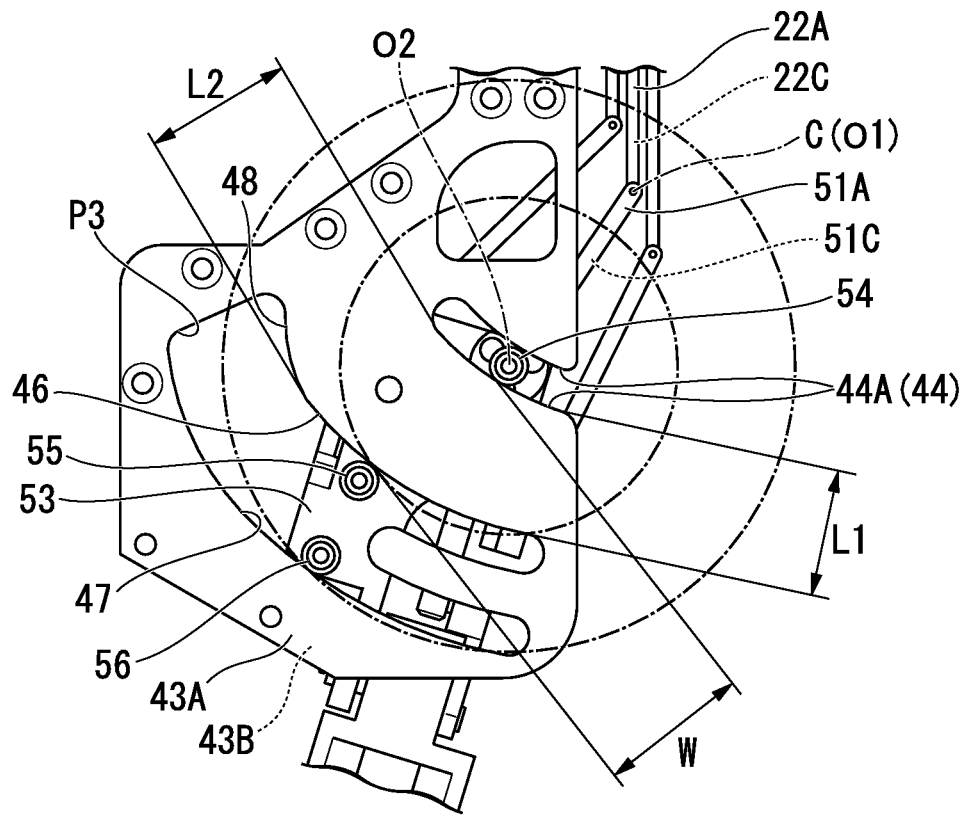
FIG. 11A and FIG. 11B are plan views that show a partial constitution of the same treatment system.
Figure 11B:
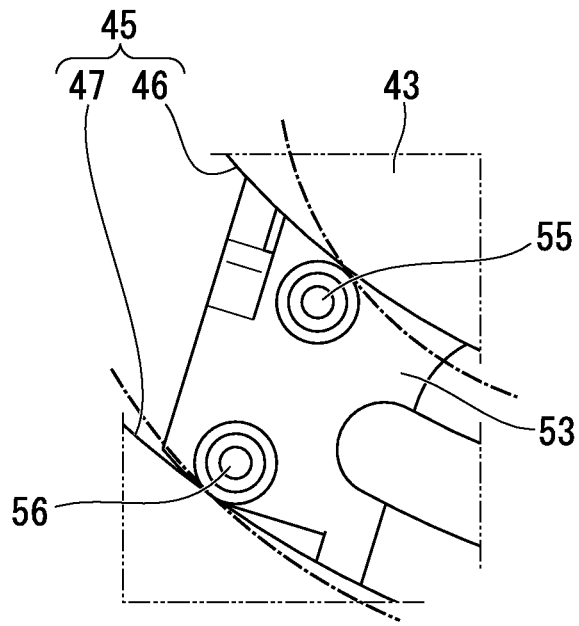

FIG. 11A is a plan view showing the configuration of a portion of the treatment system 100, and is a plan view when the operating body 41 of the arm operating portion 40 is seen toward the guide plate 43B from the guide plate 43A side. Additionally, FIG. 11B is an enlarged view showing a portion of FIG. 11A in an enlarged manner.

As shown in FIG. 11A, the first guide groove 44 has a pair of wall portions 44A for guiding the turning shaft portion 54 of the turning member 53. The shape of the pair of wall portions 44A becomes a curved surface which is curved such that the profile line when the wall portions 44A are seen from the thickness direction of the guide plate 43A makes a portion of an arc. Additionally, a straight line passing through the center of the arc in the pair of wall portions (refer to FIG. 10A) formed in each of the guide plate 43A and the guide plate 43B is a first turning center O1 around which the turning member 53 and the operating lever 58 turns. In the present embodiment, the position of the first turning center O1 becomes a position which overlaps a coupling portion C between the connecting rods 22A and 22C and the links 51A and 51C when the arm operating portion 40 when the first bending portion 32 is in a neutral state (a state where the first bending portion is not bent; refer to FIG. 2) is seen from the thickness direction of the guide plate 43A in the arm operating portion 40.

As shown in FIGS. 9A and 9B, in a state where the tip coupling portion 42, the guide plates 43A and 43B, the turning member 53, and the operating lever 58 are assembled, the above-described turning member 53 is adapted such that the turning shaft portion 54 of the turning member 53 is guided to the wall portion 44A of the first guide groove 44 and is operated to swing around the first turning center O1, between a first position P1 where the longitudinal axis direction of the operating lever 58 and the direction in which the transmission member 22 inserted through the arm body portion 21 extends coincide with each other and a second position P2 where the longitudinal axis direction of the operating lever 58 and the direction in which the transmission member 22 extends, and the turning shaft portion 54 comes into contact with the end 44B of the first guide groove 44.

Moreover, as shown in FIGS. 9A and 10A, when the coupling rod 61 is positioned at the position of the through-hole 49B by the above-described positioning portion 62, the other end 61C of the coupling rod 61 is supported by the pulling guide portion 67, the through-hole 61B is positioned at a position where the through-hole overlaps the through-hole 49B, and one end 61A of the coupling rod 61 is positioned at and fixed to the position of the end 44B of the first guide groove 44. At this time, the above-described turning member 53 is adapted so as to oscillate around the second turning center O2 with the turning shaft portion 54 as the second turning center O2 in a state where the turning shaft portion 54 is at the end 44B of the first guide groove 44.

As shown in FIGS. 10A and 10B, the second guide groove 45 is formed radially outside the arc of the first guide groove 44, and has an inner wall portion 46 located on the side relatively near first turning center O1, and an outer wall portion 47 located on the side relatively far from first turning center O1.

The first guide pin 55 and second guide pin 56 of the turning member 53 are inserted into the second guide groove 45. Additionally, a sliding member F2 which touches the external surfaces of the guide plates 43A and 43B is provided between the first guide pin 55 and the second guide pin 56, and the second guide groove 45. The sliding member F2 has elasticity, and is pressed against the guide plate 43A by the first guide pin 55 and the second guide pin 56.

As shown in FIGS. 11A and 11B, the shape of the inner wall portion 46 becomes a curved surface which is curved such that the profile line when the inner wall portion 46 is seen from the thickness direction of the guide plate 43A forms a curve. The inner wall portion 46 presses the outer peripheral surface of the first guide pin 55 of the turning member 53 to guide the turning member 53 when the turning member 53 is turned around the first turning center O1 counterclockwise as the arm operating portion 40 is seen toward the guide plate 43B from the guide plate 43A side.

In the present embodiment, the turning shaft portion 54 of the turning member 53 comes into contact with the wall portion 44A of the first guide groove 44 and the first guide pin 55 of the turning member 53 comes into contact with the inner wall portion 46 of the second guide groove 45 such that the turning shaft portion and the first guide pin are guided by the wall portions, respectively.

The distance between the inner wall portion 46 and the first guide groove 44 is shorter than the spacing W between the turning shaft portion 54 and the first guide pin 55 in the turning member 53. Additionally, as shown in FIGS. 9A and 11A, the distance between the inner wall portion 46 and the first guide groove 44 is set, and the second guide groove 45 is formed such that the distance L2 between the turning shaft portion 54 and the first guide pin 55 when the operating lever 58 is located at the second position P2 may become gradually larger than the distance L1 between the turning shaft portion 54 and the first guide pin 55 when the operating lever 58 is located at the first position P1. In addition, the maximum valve of the distance between the inner wall portion 46 and the first guide groove 44 is made approximately equal to the spacing W between the turning shaft portion 54 and the first guide pin 55 in the turning member 53.

As shown in FIGS. 10A and 10B, the shape of the outer wall portion 47 becomes a curved surface which is curved such that the profile line when the inner wall portion 46 is seen from the thickness direction of the guide plate 43A forms a curve. The outer wall portion 47 presses the second guide pin 56 of the turning member 53 to guide the turning member 53 when the turning member 53 is turned around the first turning center O1 clockwise as the arm operating portion 40 is seen toward the guide plate 43B from the guide plate 43A side.

Additionally, the end P3 of the second guide groove 45 opposite to the first position P1 is provided with an escape portion 48 in which the inner wall portion 46 and the outer wall portion 47 are formed so as to have different shapes. The escape portion 48 is formed so as to be depressed closer to the first guide groove 44 than the inner wall portion 46.

As for the operation when the treatment system 100 of the present embodiment with the configuration described above is used, the operation of the manipulator 1 will be mainly described with reference to FIGS. 12 to 24.

Figure 12:
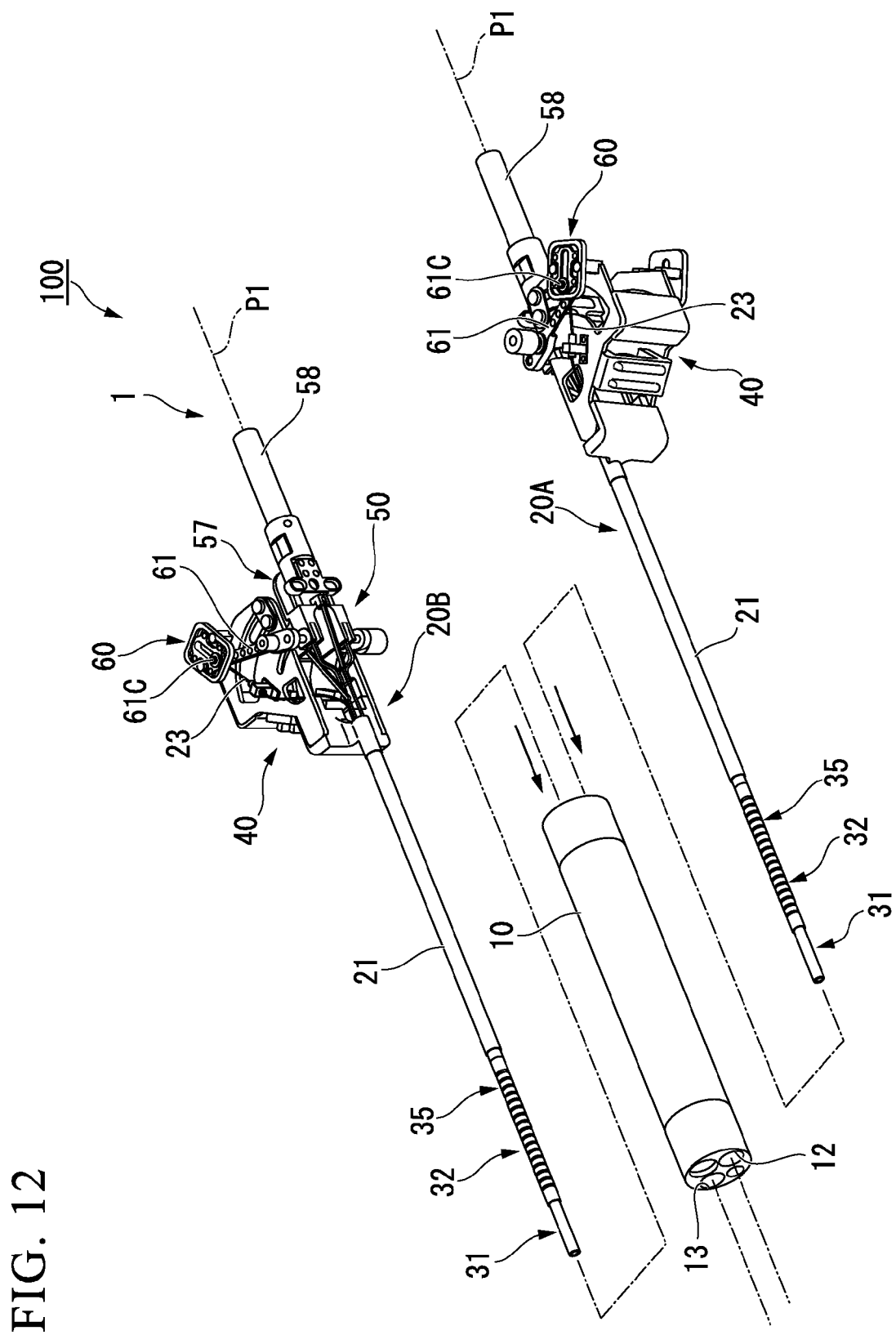
FIG. 12 is an action explanation drawing for explaining the action during use of the same treatment system.

FIG. 12 is an operation explanatory view explaining the operation of assembling the treatment system 100 in a form when the system is used. As shown in FIG. 12, when the treatment system 100 is used, first, an operator inserts the first arm 20A through the channel 12 of the insertion portion 10, and inserts the second arm 20B through the channel 13. At this time, in the arm operating portions 40 of the first arm 20A and the second arm 20B, the operating levers 58 are brought into the state of being moved toward the first position P1. When the operating lever 58 is at the first position P1, in the first bending operating portion 50, the operating lever 58 is aligned such that the vertical movement guide pins 59A are located at the intermediate portion of the through-hole 57A of the vertical movement guide 57 (refer to FIGS. 5, 20A, and 20B). Thereby, the transmission member 22 coupled to the first bending operating portion 50 is located at a linear neutral position where the first bending portion 32 is not bent.

Additionally, when the operating lever 58 is at the first position P1, in the second bending operating portion 60, the other end 61C of the coupling rod 61 is located at one end 68A of the through-hole 68 of the pulling guide portion 67, and the second operating wire 23 coupled to the other end 61C of the coupling rod 61 is not pulled (refer to FIG. 9A and FIG. 9B). For this reason, the second bending portion 35 is brought into a linear state due to its own restoring force.

Accordingly, the first bending portion 32, the second bending portion 35, and the arm body portion 21 become linear. In this state, the operator inserts the first arm 20A and the second arm 20B into the channel 12 and the channel 13, respectively, from the tip hard portion 31 side.

Figure 13:
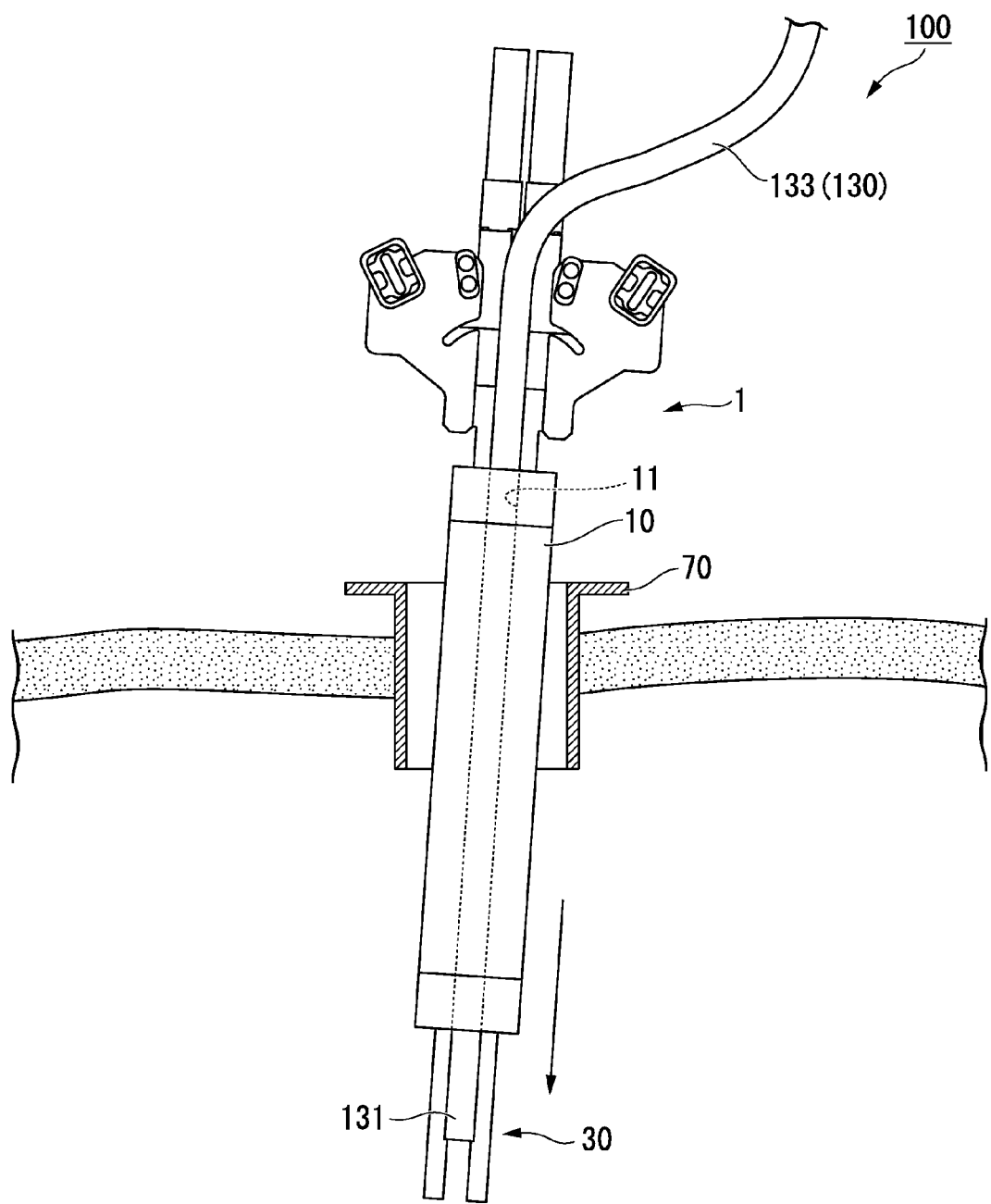
FIG. 13 is an action explanation drawing for explaining the action during use of the same treatment system.

FIG. 13 is an operation explanatory view showing one process when the treatment system 100 is used. As shown in FIG. 13, the operator applies, for example, small incision to a patient's abdominal wall, and inserts a trocar 70 into which the insertion portion 10 of the treatment system 100 can be inserted. The operator inserts the treatment system 100 into the body cavity from the arm tip portion 30 side via the trocar 70 after performing pneumoperitoneum or the like if needed. At this time, the insertion portion 133 of the endoscope 130 is inserted into the channel 11 of the insertion portion 10, the imaging portion 131 is made linear along the arm tip portion 30, and the arm tip portion 30 is guided to a part to be treated in the body cavity, watching an image imaged by the imaging portion 131.

Figure 14:
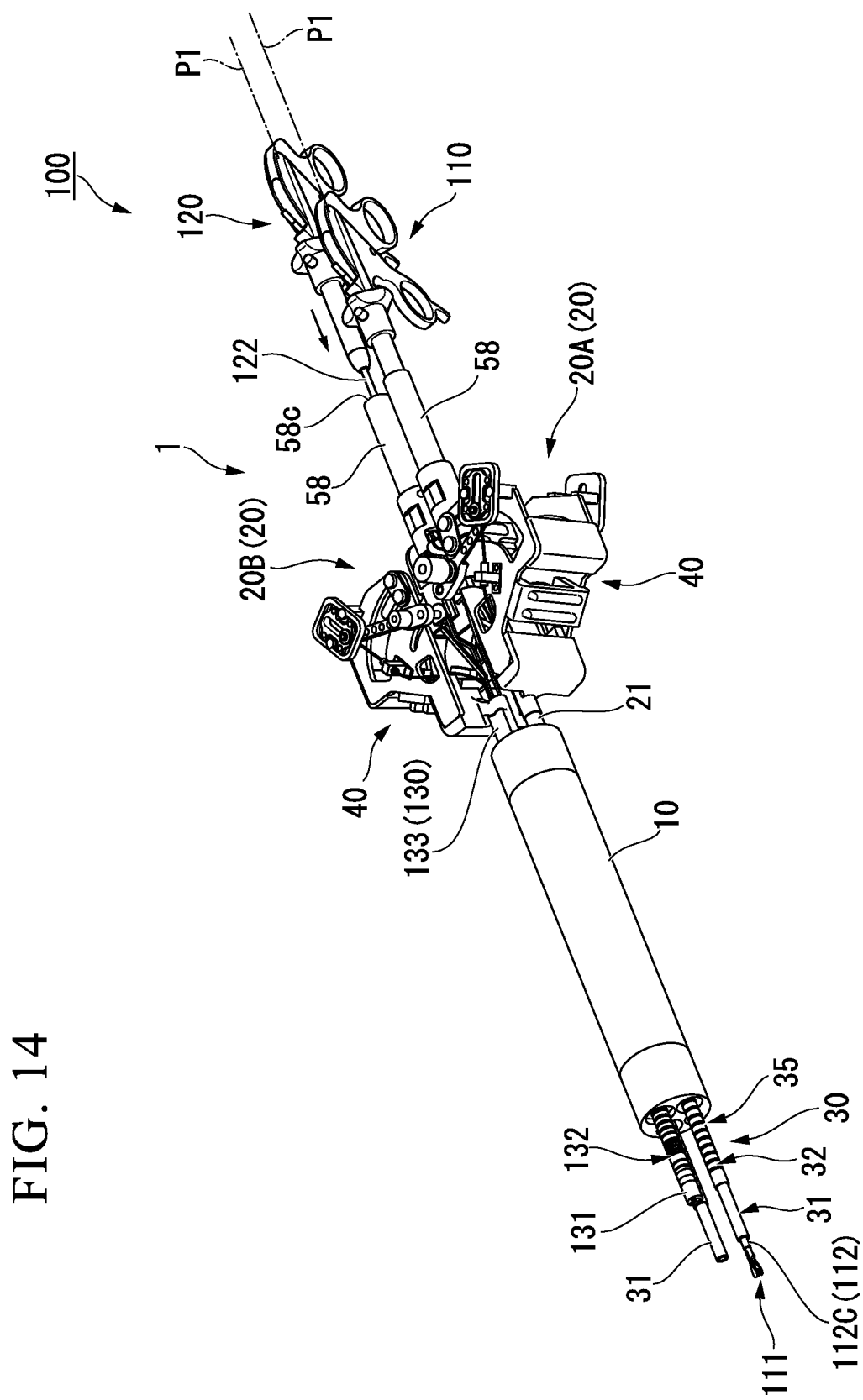
FIG. 14 is an action explanation drawing for explaining the action during use of the same treatment system.

FIG. 14 is an operation explanatory view showing one process when the treatment system 100 is used. As shown in FIG. 14, if the arm tip portion 30 has been guided to the object to be treated, the operator inserts the treatment tools 110 and 120 into the body cavity through the treatment tool insertion port 58C of the operating lever 58.

When the operating lever 58 is located at the first position P1, the operating lever 58 and the arm body portion 21 are coaxially aligned. Additionally, the first bending portion 32 and the second bending portion 35 are not bent, but linear. Accordingly, when the operating lever 58 is at the first position P1, a duct for allowing the insertion portions 112 and 122 of the treatment tools 110 and 120 to be inserted therethrough from the treatment tool insertion port 58C of the operating lever 58 to the tip hard portion 31 of the arm tip portion 30 becomes linear.

For this reason, the treatment portion 111 inserted from the treatment tool insertion port 58C of the operating lever 58 is paid out from the tip of the tip hard portion 31 through the insides of the operating lever 58, the turning member 53, the arm body portion 21, and the arm tip portion 30 in this order. The treatment tool 120 is similarly paid out from the tip of the tip hard portion 31.

Figure 15A:
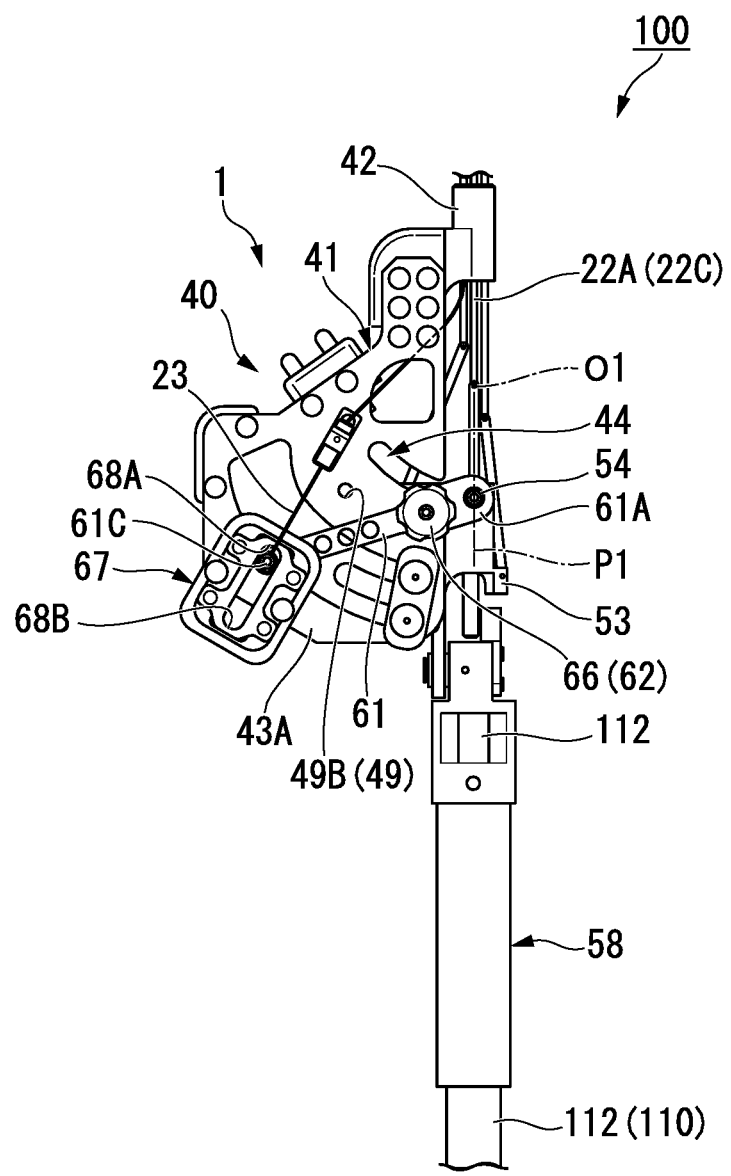
FIG. 15A, FIG. 15B, and FIG. 15C are action explanation drawings for explaining the action during use of the same treatment system.
Figure 15B:
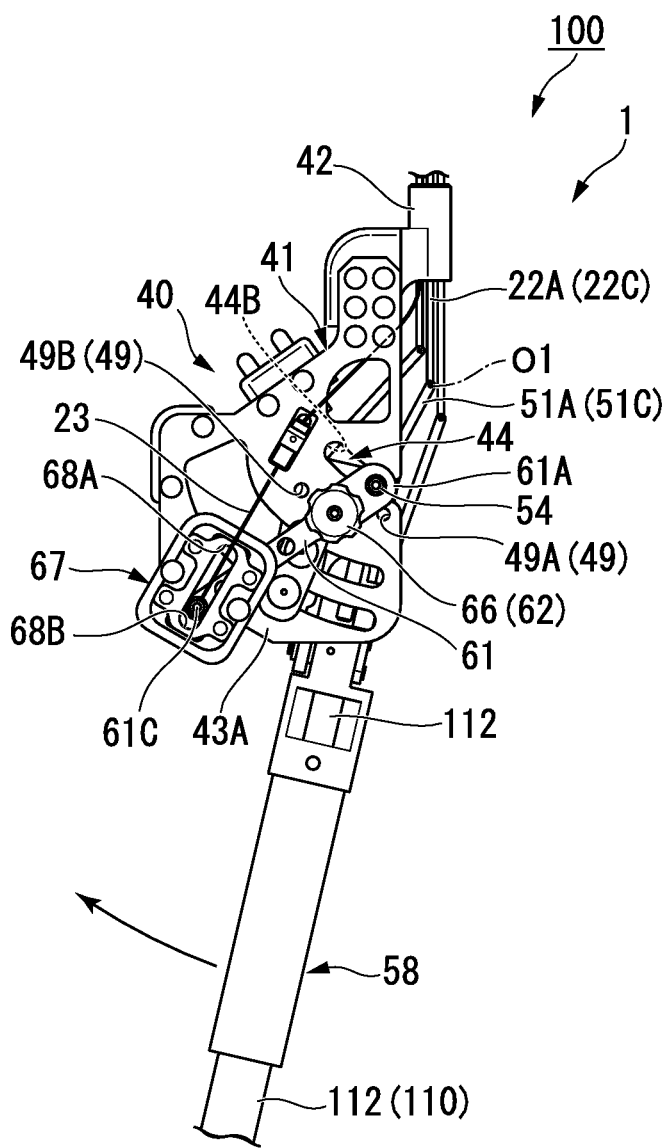
Figure 15C:
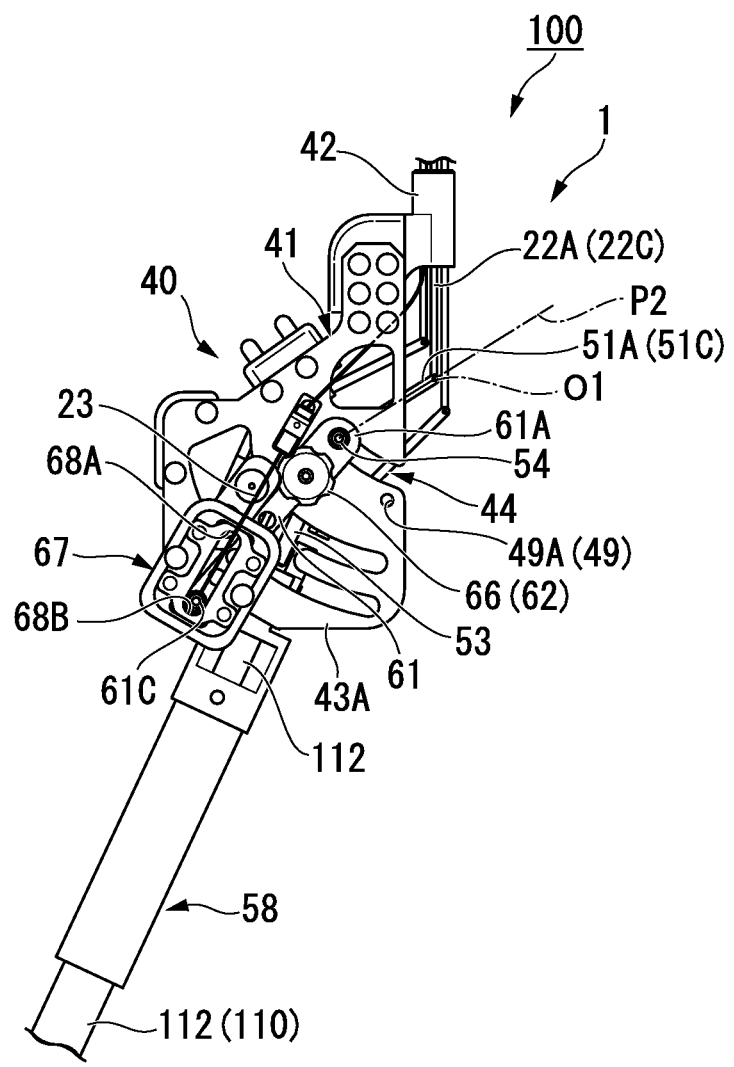

FIGS. 15A to 15C are operation explanatory views showing one process when the treatment system 100 is used. As shown in FIG. 15A, the operator moves the operating lever 58 relative to the operating body 41 from an initial state where the operating lever 58 is at the first position P1, and performs a swing operation of the turning shaft portion 54 of the turning member 53 around the first turning center O1. When the operating lever 58 is at the first position P1, although the tip engaging portion 63A (refer to FIG. 8B) of the positioning pin 63 in the positioning portion 62a fits to the dent 49A of the guide plate 43A, the dent 49A is substantially hemispherical. Thus, by applying a force so as to turn the operating lever 58, the fitting between the tip engaging portion 63A and the dent 49A can be released even if not in contact with the pin operating portion 66. Then, as shown in FIG. 15B, the turning shaft portion 54 advances into the first guide groove 44.

As shown in FIGS. 15B and 15C, when the turning shaft portion 54 has moved to the end 44B of the first guide groove 44, the link 51A and the link 51C of the link portion 51 are turned around the first turning center O1. Accordingly, even if the turning member 53 is turned around the first turning center O1, the connecting rod 22A and the connecting rod 22C do not move between the first position P1 and the second position P2. As a result, the first joint ring 33 connected to the connecting rod 22A and the connecting rod 22C via the angle wire 34A and the angle wire 34C is not pulled, and the first bending portion 32 is not bent in the vertical direction.

FIGS. 16A to 16C are explanatory views showing the principle of operation of the first bending operating portion 50 when the operating lever 58 is moved toward the second position P2 from the first position P1 side. In addition, FIG. 16B is an explanatory view explaining the positional relationship of the first bending operating portion 50 when the turning member 53 is not turned around the second turning center O2, and is not a drawing showing an actual operation when the operation of moving the operating lever 58 toward the second position P2 from the first position P1 side in the treatment system 100 of the present embodiment is performed.

Additionally, the lines indicated by the reference numerals L1 and L2 in FIGS. 16A to 16C represent the positions of the tip and proximal end of the respective connecting rods when the operating lever 58 is at the first position P1.

When the operating lever 58 is moved toward the second position P2 as shown in FIG. 16C from the first position P1 shown in FIG. 16A, as the first guide pin 55 and the second guide pin 56 are guided to the inner wall portion 46 and outer wall portion 47 of the second guide groove 45, the turning member 53 is turned counterclockwise around the second turning center O2 as seen toward the guide plate 43B from the guide plate 43A side. At this time, the amount of pulling by which the connecting rod 22B is pulled via the link 51B as the turning member 53 is turned clockwise around the first turning center O1 as seen toward the guide plate 43B from the guide plate 43A side (refer to FIG. 16B), and the amount of push-out by which the connecting rod 22B is pushed out via the link 51B as the turning member 53 is turned counterclockwise around the second turning center O2 as seen toward the guide plate 43B from the guide plate 43A side are set to be equal to each other. As a result, even if the turning member 53 is turned clockwise around the first turning center O1, the connecting rod 22B does not operate to advance and retract inside the arm body portion 21 between the first position P1 and the second position P2.

Similarly, the amount of push-out by which the connecting rod 22D is pushed out via the link 51D as the turning member 53 is turned clockwise around the first turning center O1 as seen toward the guide plate 43B from the guide plate 43A side (refer to FIG. 16B), and the amount of pulling by which the connecting rod 22D is pulled via the link 51D as the turning member 53 is turned counterclockwise around the second turning center O2 as seen toward the guide plate 43B from the guide plate 43A side are set to be equal to each other. As a result, even if the turning member 53 is turned around the first turning center O1, the connecting rod 22D does not operate to advance and retract inside the arm body portion 21 between the first position P1 and the second position P2.

Accordingly, even if the turning member 53 is turned around the first turning center O1, the connecting rods 22B and 22D do not operate to advance and retract between the first position P1 and the second position P2, the first joint ring 33 connected to the connecting rod 22B and the connecting rod 22D via the angle wire 34B and the angle wire 34D is not pulled, and the first bending portion 32 is not bent in the right-and-left direction.

In this way, even if the turning member 53 is turned around the first turning center O1 from the first position P1 to the second position P2, the first bending portion 32 is not bent but the linear shape thereof is maintained.

At this time, in the arm operating portion 40, the magnitude $\theta_1$ of an angle that the tip 58A of the operating lever 58 makes with a straight line X which is parallel to the longitudinal axis of the transmission member 22, and passes through the first turning center O1, and the magnitude $\theta_2$ formed an angle that the proximal end 58B of the operating lever 58 with respect to the straight line X become $\theta_1 > \theta_2$. That is, when the operating lever 58 is turned, the turning member 53 is turned around the first turning center O1, and simultaneously, the turning member 53 is turned in the opposite direction around the second turning center O2. Thus, the proximal end 58B of the operating lever 58 is turned later than the tip 58A of the operating lever 58.

On the other hand, as shown in FIGS. 15B and 15C, when the operating lever 58 is moved toward the second position P2 from the first position P1 side, the coupling rod 61 is moved toward the second position P2 by the turning shaft portion 54 of the turning member 53. Then, the other end 61C of the coupling rod 61 moves to the other end 68B from one end 68A along the through-hole 68 of the pulling guide portion 67. Thereby, the second operating wire 23 fixed to the other end 61C of the coupling rod 61 is pulled toward the other end 68B of the through-hole 68.

FIGS. 17A and 17B are perspective views showing the operation when the treatment system 100 is used, and showing the vicinity of the arm tip portion 30 in an enlarged manner.

When the second operating wire 23 is pulled by the coupling rod 61 as shown in FIGS. 15A and 15C, the second bending portion 35 coupled to the tip of the second operating wire 23 is bent as shown in FIGS. 17A and 17B. When bending operation of the second bending portion 35 provided at the first arm 20A and the second arm 20B is performed, a state where the separation distance between the first bending portion 32 and the treatment portions 111 and 121 in the arm tip portion 30 is increased more than that at a normal time and manipulation is easily performed is brought (the state in question is referred to as "tri-angulation" below).

In each of the first arm 20A and the second arm 20B, the second operating wire 23 whose tip is fixed to the second joint ring 36, as already described with reference to FIGS. 9A and 9B, is supported in a state where the second operating wire has been pulled toward the arm operating portion 40 by the toggle mechanism of the second bending operating portion 60, and is fixed to the guide plates 43A and 43B of the operating body 41 by the positioning portion 62. If needed, the operator may rotate the pin operating portion 66 of the positioning portion 62 shown in FIG. 8B around an axis with respect to the fixed portion 65 so as to prevent the positioning pin 63 from slipping off the through-hole 49B. In this case, the second bending portion 35 and the operating lever 58 can be kept from deviating in the midst of the treatment using the treatment portions 111 and 121.

In this way, simply by moving the operating lever 58 to the second position P2 from the first position P1, the operating lever 58 is arranged in a V-shape in which the treatment tool 110 and the treatment tool 120 are easily operated, and the operating portions 113 and 123 of the treatment tools 110 and 120 do not collide with each other, and the arm portion 20 is deformed into the state of the triangulation shown in FIG. 17B from the initial positional relationship shown in FIG. 17A.

The operation of bending the first bending portion 32 in the state of the triangulation will be described below. First, the operation of bending the first bending portion 32 to right and left will be described with reference to FIGS. 18 to 19C.

Figure 18:
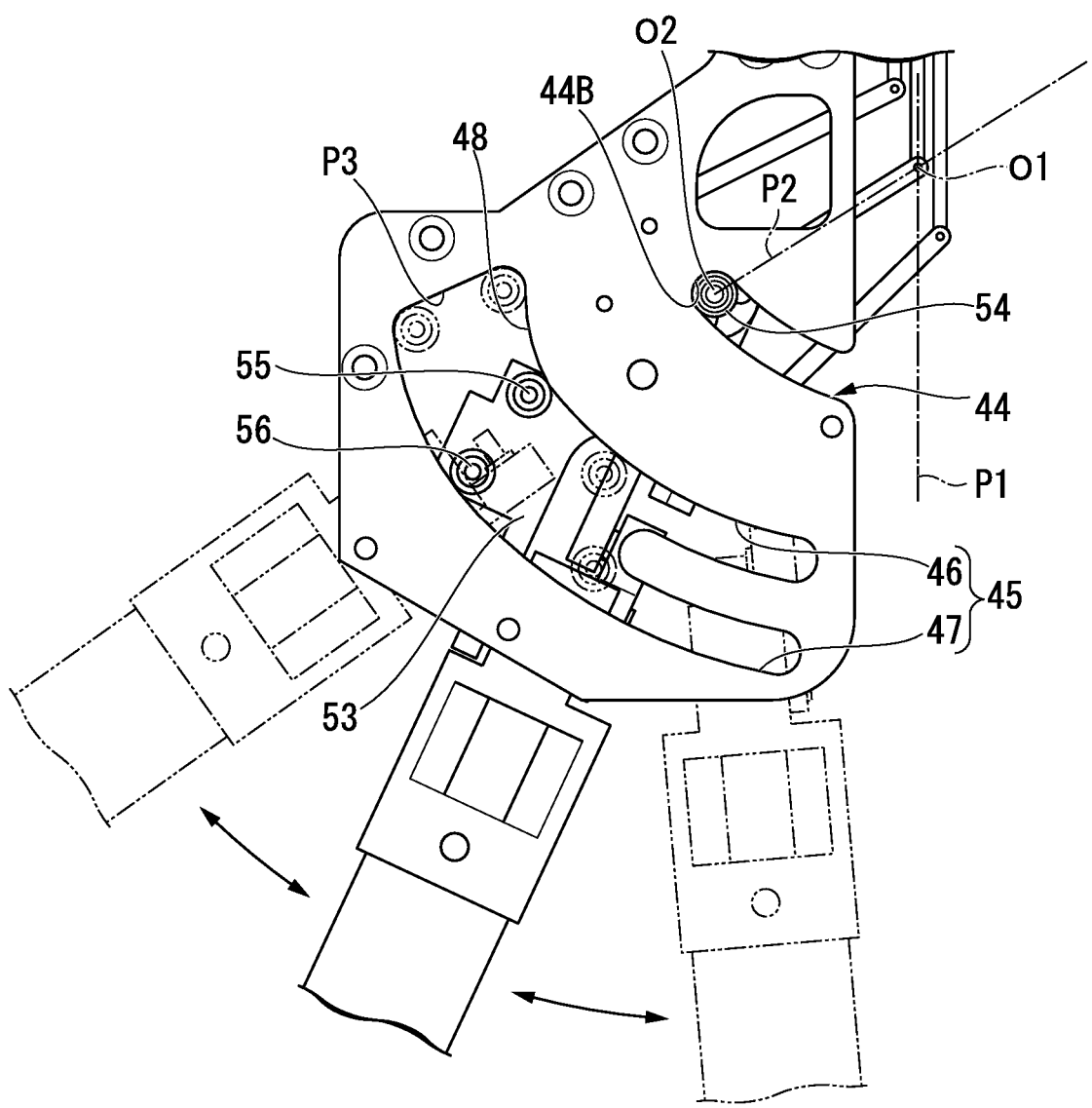
FIG. 18 is an explanation drawing for explaining the behavior of the operation portion during use of the same treatment system.

FIG. 18 is an operation explanatory view explaining the operation of bending the first bending portion 32, in the state of the triangulation. As shown in FIG. 18, the operator can move the operating lever 58, for example, toward the end P3 or the first position P1 from a state where the operating lever 58 is at the second position P2. At this time, since the turning shaft portion 54 is positioned at the end 44B of the first guide groove 44, the turning shaft portion 54 cannot be turned around the first turning center O1. On the other hand, the turning member 53 can be turned around the second turning center O2 which is the central axis of the turning shaft portion 54. In a case where the turning member 53 moves, for example, toward the first position P1, around the second turning center O2, the first guide pin 55 and the second guide pin 56 are moved toward the first position P1, and the turning member 53 can be oscillated within a predetermined range between the inner wall portion 46 and outer wall portion 47 of the second guide groove 45. Additionally, in a case where the turning member 53 moves, for example, toward the end P3 around the second turning center O2, the first guide pin 55 and the second guide pin 56 can be moved toward the end P3, and can be moved along the escape portion 48 or within a predetermined range inside the escape portion 48.

FIGS. 19A to 19C are operation explanatory views explaining the operation of the first arm 20A when a turning operation of the turning member 53 around the second turning center O2 is performed. For example, as shown in FIG. 19B, when the turning member 53 is turned toward the end P3 (refer to FIG. 18) around the second turning center O2, in the link portion 51, the links 51A and 51C do not operate, but the link 51B is pulled and the link 51D is pushed out. Thereby, the angle wire 34B is pulled by the connecting rod 22B, and a bending operation of the first bending portion 32 is performed rightward by the angle wire 34B in plan view shown in FIG. 19B. Similarly, as shown in FIG. 19C, when the turning member 53 is turned toward the first position P1 (refer to FIG. 18) around the second turning center O2, bending operation of the first bending portion 32 is performed leftward in plan view shown in FIG. 19B.

The operation of bending the first bending portion 32 in the vertical direction will be described below with reference to FIGS. 20A to 23.

FIGS. 20A to 22B are operation explanatory views explaining the operation of bending the first bending portion 32.

Figure 20A:
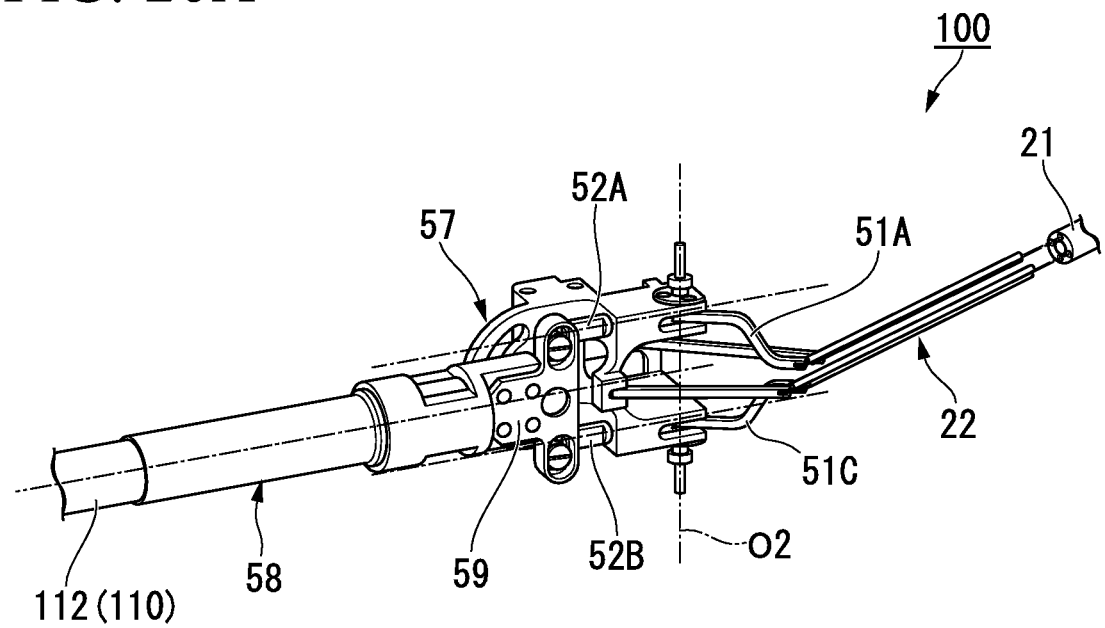
FIG. 20A and FIG. 20B are perspective views that show the operation portion when the lever is at the neutral position during use of the same treatment system.
Figure 20B:
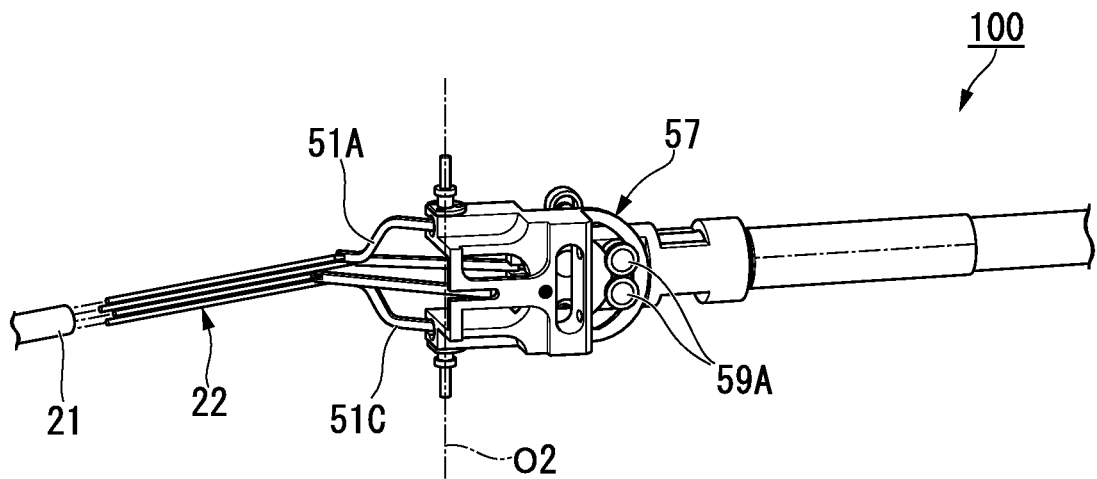

As shown in FIGS. 20A and 20B, when the first bending portion 32 is brought into a neutral state where the first bending portion is not bent in the vertical direction, the operating lever 58 is matched with a direction parallel to the axial direction of the first slider 52A and second slider 52B of the slider link portion 52 such that both a connected portion between the link 51A and the first slider 52A, and a connected portion between the link 51C and the second slider 52B are on the second turning center O2. At this time, since the vertical movement guide 57 is pinched by the vertical movement guide pins 59A and the connecting portion 59 via the sliding members F1, even if an operator's hand is released from the treatment tools 110 and 120 inserted into the operating lever 58, the position of the operating lever 58 relative to the turning member 53 is maintained.

Figure 21A:
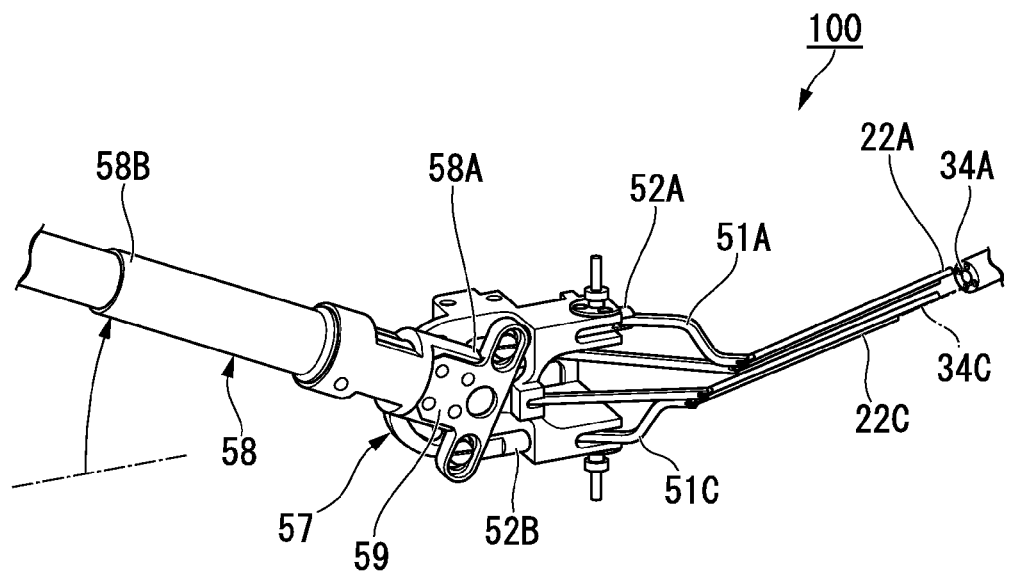
FIG. 21A and FIG. 21B are perspective views that show the operation portion when the lever has been operated in the upper direction during use of the same treatment system.
Figure 21B:
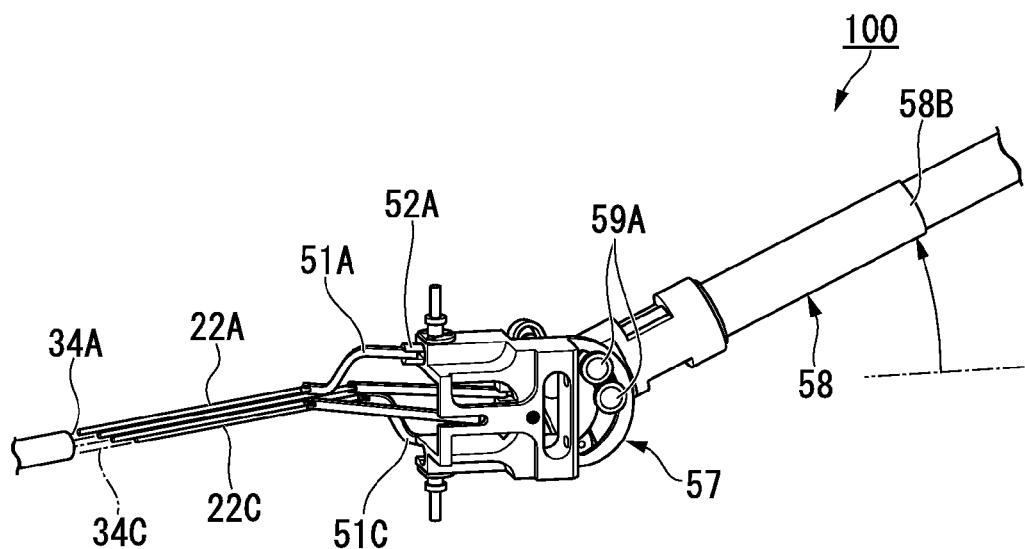

As shown in FIGS. 21A and 21B, in order to bend the first bending portion 32 downward, the proximal end of the operating lever 58 is pulled up such that the distal side of the operating lever 58 becomes the downside relatively. Then, the first slider 52A is pushed into the distal side, and the second slider 52B is pulled out to the proximal side. Thereby, the connecting rod 22A is pushed out to the distal side via the link 51A, and the connecting rod 22C is pulled out to the proximal side via the link 51C. Then, in the arm tip portion 30, the angle wire 34C fixed to the tip of the connecting rod 22C is pulled, and the first bending portion 32 is bent downward.

Figure 22A:
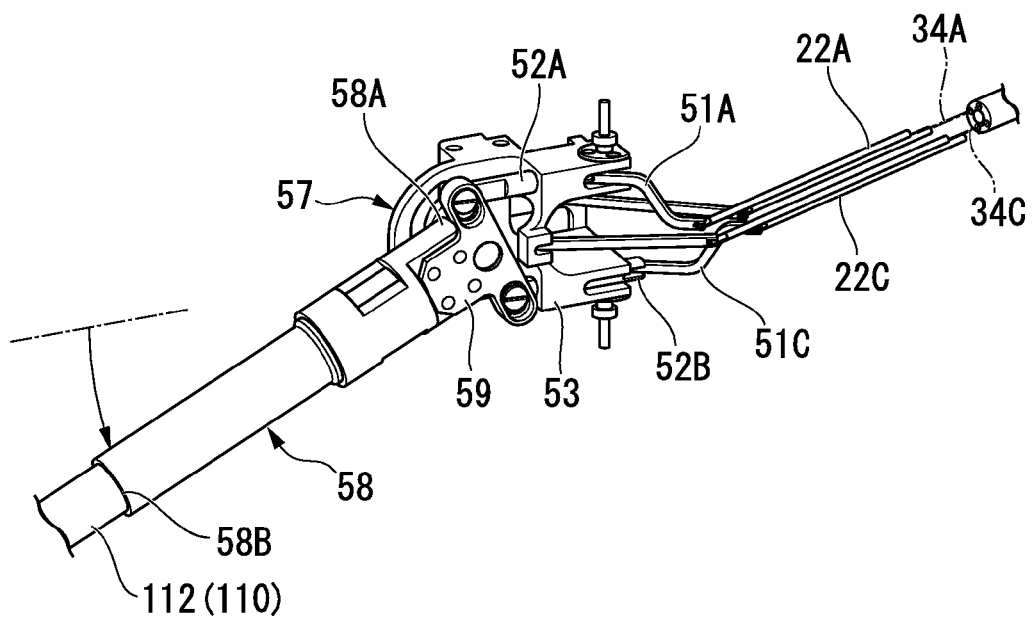
FIG. 22A and FIG. 22B are perspective views that show the operation portion when the lever has been operated in the lower direction during use of the same treatment system.
Figure 22B:
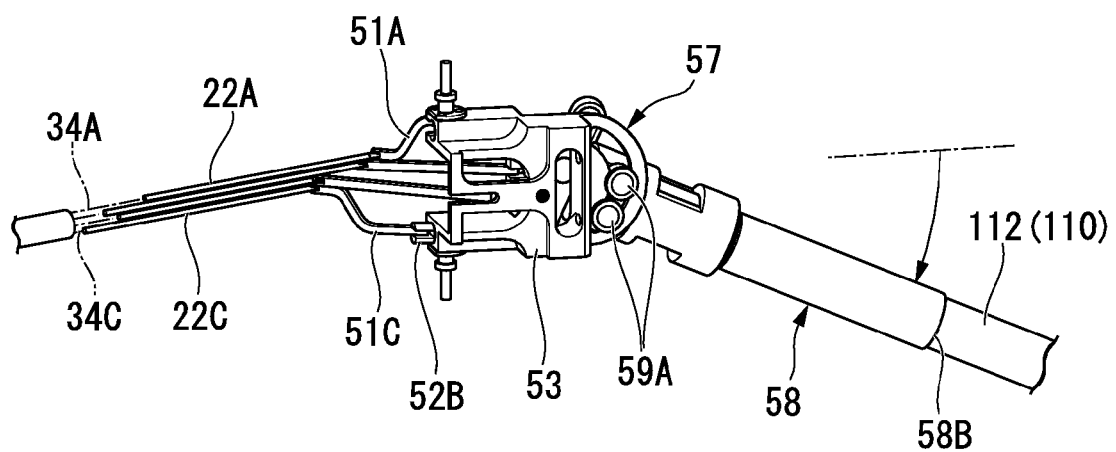

On the other hand, as shown in FIGS. 22A and 22B, in order to bend the first bending portion 32 upward, the proximal end of the operating lever 58 is pulled down such that the distal side of the operating lever 58 becomes the upside relatively. Then, the first slider 52A is pulled out to the proximal side, and the second slider 52B is pushed out to the distal side. Then, contrary to the above-described operation, the angle wire 34A fixed to the tip of the connecting rod 22A is pulled, and the first bending portion 32 is bent downward.

Although the bending operation of the first bending portion 32 and the second bending portion 35 in the first arm 20A has been described above, the bending operation of the first bending portion 32 and the second bending portion 35 can be similarly performed even in the second arm 20B. Then, as shown in FIG. 23, the treatment using the treatment portions 111 and 121 of the treatment tools 110 and 120 can be performed using the first arm 20A and the second arm 20B.

Figure 23:
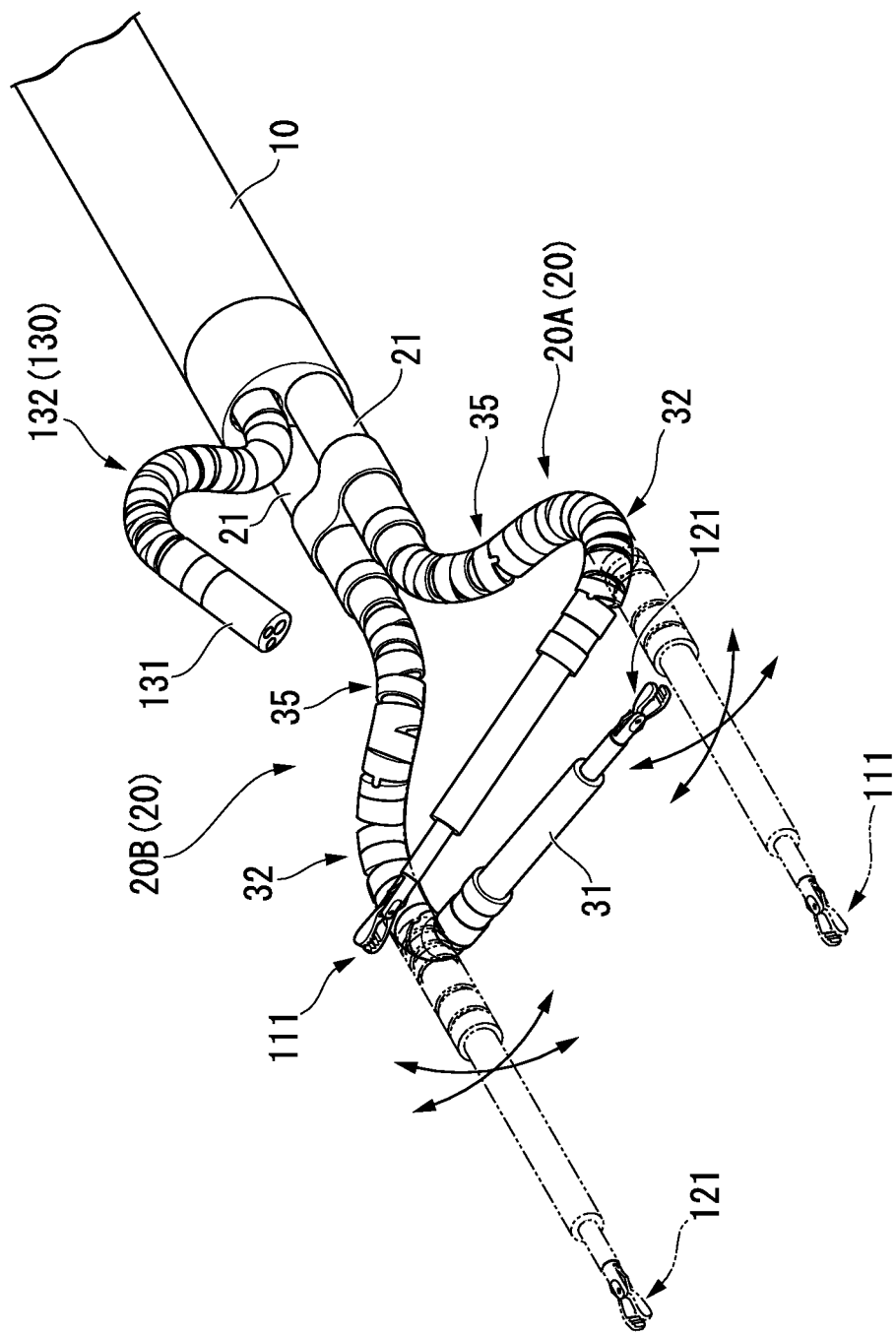
FIG. 23 is an action explanation drawing that shows the action of the distal end portion during use of the same treatment system.

In addition, in order to facilitate the observation of an object to be treated, as shown in FIG. 23, the bending portion 132 of the endoscope 130 is bent, so that the orientation of the visual field of the imaging portion 131 can also be appropriately changed.

Meanwhile, in the midst of performing a treatment on an object to be treated, a treatment tool different from the treatment tool 110 and the treatment tool 120 is used after being attached to the arm portion 20. In this case, the operation of removing a treatment tool from any one or both of the first arm 20A and the second arm 20B is performed.

Figure 24:
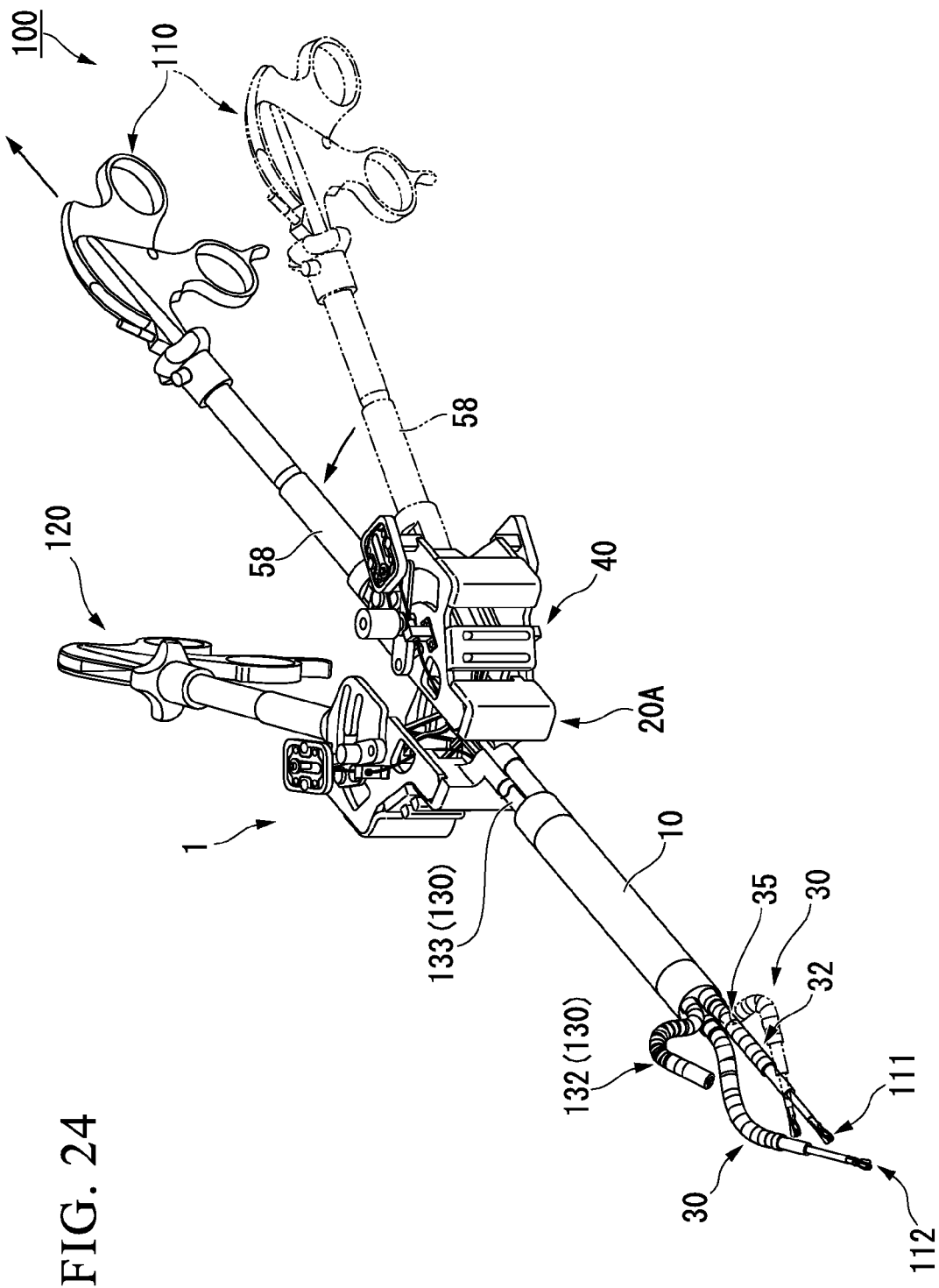
FIG. 24 is an action explanation drawing for describing the operation of removing a treatment tool during use of the same treatment system.

FIG. 24 is an operation explanatory view explaining the operation of removing the treatment tool 110 from the manipulator 1 when the treatment system 100 is used. When the treatment tool 110 is removed from the manipulator 1, the operating lever 58 is moved toward the first position P1 from the second position P2 side, as shown in FIGS. 15C, 15B, and 15A, in an order reverse to the operation of attaching the treatment tool 110 to the manipulator 1. Then, the turning member 53 is guided by the first guide groove 44 and the second guide groove 45, is turned toward the first position P1 around the first turning center O1, and is turned toward the second position P2 around the second turning center O2. Thereby, as shown in FIG. 24, the operating lever 58 moves to the same linear position as that when the treatment tool 110 is inserted, and the bending of the second bending portion 35 is released and returns to the linear positional relationship from the state of the triangulation. The operator can remove the treatment tool 110 in this state, and can insert and use other treatment tools similarly.

Conventionally, a treatment system is known which includes a hard insertion portion inserted into a body cavity, and an arm portion inserted into the insertion portion, and which performs a treatment within the body cavity, using a treatment tool inserted into the arm portion.

In such a conventional treatment system, as for the treatment tool used after being attached to the treatment system, a hard portion may be provided at a portion of the insertion portion in order to sufficiently transmit the amount of a pulling force to the treatment portion. In order to attach such a treatment tool to the conventional treatment system, it is necessary to deform the treatment system into a linear state which is different from a shape suitable for performing a treatment, and to deform the treatment system into a shape for performing a treatment during treatment.

In the conventional treatment system, for example, a tip portion of the arm portion may be configured so as to be bendable. Specifically, the arm portion may have a first bending portion provided on the distal side of the tip portion of the arm portion, and a second bending portion provided closer to the proximal side than the first bending portion. When a treatment tool is attached to the treatment system having such an arm portion, there is a case in which operating portions are separated and the operating portions are aligned so as to facilitate the operation of the treatment tool and so as not to interfere with the operation of mutual operating portions during the operation of the operating portions of the treatment tool. In this case, however, as a portion of the tip portion (for example, the first bending portion) of the arm portion is bent by the alignment operation, the initial position when a treatment is performed using the treatment tool within a body cavity may have a positional relationship in which it is not easy to perform a treatment.

According to the treatment system 100 and manipulator 1 of the present embodiment, the first turning center O1 and the second turning center O2 around which the operating lever 58 is turned are set, the turning operation around the first turning center O1 and the turning operation around the second turning center O2 are synthesized by the first guide groove 44 and the second guide groove 45 which are formed in the operating body 41, and the operating lever 58 is moved to the second position P2 from the first position P1. Thus, even if an operator moves the operating lever 58 to the second position P2 from the first position P1, the first bending portion 32 can be maintained in a linear state.

In addition, according to the treatment system 100 and manipulator 1 of the present embodiment, the arm operating portion 40 which operates the first arm 20A and the second arm 20B in the body is provided with the operating lever 58 for inserting the treatment tool therethrough, and the first arm 20A and the second arm 20B are provided with the first bending portion 32 and the second bending portion 35. Also, the first bending portion 32 and the second bending portion 35 are bent due to operating the arm operating portion 40. Thus, the arm operating portion 40 and the bending portion can be arranged linearly when the treatment tool is replaced by another, and the pair of the arm operating portion 40 can be away from each other when the operator operates the treatment tool. An undesirable operation of the bending portion for the operator can be prevented when the operator operates the arm operating portion 40.

Additionally, in the conventional treatment system, in order for the treatment system to maintain the treatment portion at the initial position even if the treatment tool is set to the orientation which is easy to use, it is necessary to perform strict positional adjustment in the bending operating portion of the treatment system, thereby configuring the treatment system.

According to the treatment system 100 and manipulator 1 of the present embodiment, the orientation of the turning member 53 in each of the first position P1 and the second position P2 can be determined by the first guide groove 44 and the second guide groove 45 which are formed in the arm operating portion 40. Thus, the degree of freedom in design when the transmission member 22 and the link portion 51 are arranged can be enhanced.

Additionally, in the conventional treatment system, in order to deform the arm in the state of the triangulation, it is necessary to bend the arm by an operation different from performing setting such that the treatment tool is brought to a position which is easy to use.

According to the treatment system 100 and manipulator 1 of the present embodiment, the second operating wire 23 can be pulled when the second bending operating portion 60 provided at the arm operating portion 40 operates in conjunction with the operation of the operating lever 58, and the operating lever 58 moves to the second position P2. Thus, the handling of the treatment system 100 can be simplified.

Moreover, since the second bending operating portion 60 can constrain the second operating wire 23 in the pulled state by the toggle mechanism, the amount of a pulling force when the second operating wire 23 is pulled can be increased. Thereby, when the treatment tools 110 and 120 are attached to the arm portion 20 and a treatment is performed within a body cavity, even if an external force, such as torsion, is transmitted to the second bending portion 35, the bending state of the second bending portion 35 can be maintained and the triangulation can be secured.

Although the preferable embodiments of the present invention have been described hitherto, the present invention is not limited thereto. Additions, omissions, substitutions, and other modifications can be made without departing from the concept of the present invention.

For example, the shapes of the first guide groove 44 and second guide groove 45 are not limited to the above-described shapes. The shapes of the first guide groove 44 and second guide groove 45 can be appropriately designed, for example, by performing simulation or the like such that the relative positions of the four connecting rods 22A to 22D are not mixed up in the axial direction, when the operating lever 58 is moved toward the second position P2 from the first position P1.

Additionally although the example in which the position of the first turning center O1 is set to a position which coincides with the connected portions between the connecting rods 22A and 22C and the links 51A and 52C when the first bending portion 32 is not bent has been shown in the above-described embodiment, the present invention is not limited thereto. The position of the first turning center can be set to a position which has deviated closer to the distal side than the position of the first turning center O1. In this case, the connecting rods 22A to 22D can be pulled to the proximal side by turning the turning member 53 around the first turning center O1, with the positions of the tips of the connecting rods 22A to 22D aligned. Thereby, sagging of the angle wires 34A to 34D of the first bending portion 32 is prevented, and when the first bending portion 32 is in a linear state, the force (pretension) of pulling the distal side of the first bending portion 32 in the direction of the proximal end can be applied. Then, wobbling of the first bending portion 32 resulting from the clearance between parts in the first bending portion 32 can be reduced, and the response of the first bending portion 32 to the operation of the first bending operating portion 50 can be enhanced.

In addition, the present invention is not limited by the above description and is limited by only the scope of the appended claims.

The present invention may be appropriately applied to medical devices for performing a treatment in a body. Additionally, the present invention can also be applied to, for example, industrial manipulators, without being limited to medical applications.

What is claimed is:

1. A medical manipulator comprising:
   a longitudinal member which extends in a longitudinal axis direction;
   an arm body portion provided at a distal end of the longitudinal member;
   a first bending portion disposed at a distal end portion of the arm body portion;
   a second bending portion disposed at the distal end portion of the arm body portion and disposed at a more proximal side than the first bending portion;
   an angle wire which has a distal end part fixed to the first bending portion and has a proximal end part, the angle wire being movably inserted into the arm body portion;
   a connecting rod which is connected to the proximal end part of the angle wire, the connecting rod being movably inserted into the arm body portion;
   an operating wire fixed to the second bending portion and movably inserted into the arm body portion; and
   an arm operating portion including a guide member which is fixed to a proximal end part of the arm body portion,
   wherein the arm operating portion has:
     a link portion having a first end part of the link portion which is rotatably connected to a proximal end part of the connecting rod;
     a turning member rotatably connected to a second end part of the link portion; and
     an operating lever connected to the turning member,
   wherein the turning member has:
     a rotating shaft which is slidably supported by the guide member so as to rotate around a coupling portion in accordance with an operation of the operating lever, the coupling portion at which the connecting rod and the link portion are connected; and a guided member which is slidably engaged by the guide member so as to rotate around the rotating shaft in accordance with an operation of the operating lever, wherein the connecting rod is configured such that a position of the connecting rod in the longitudinal axis direction is fixed while the turning member rotates around the coupling portion and the turning member rotates around the rotating shaft in a direction opposite to a rotation direction which the turning member rotates around the coupling portion by operating the operating lever, wherein the operating wire is configured to be pulled to the arm operating portion side by which the turning member rotates around the coupling portion and rotates around the rotating shaft in a direction opposite to the direction in which the turning member rotates around the coupling portion by operating the operating lever, and wherein the second bending portion is bent by being pulled by the operation wire to the arm operating portion side.

2. The medical manipulator according to claim 1, wherein the guide member has:
- a first guide groove formed by hollowing out the guide member such that the rotating shaft slides in a state of engaging with the first guide groove; and
- a second guide groove formed by hollowing out the guide member such that the guided member slides in a state of engaging with the second guide groove.

3. The medical manipulator according to claim 2, wherein each of the first guide groove and the second guide groove are bent so as to form an arc shape.

4. The medical manipulator according to claim 2, wherein the rotating shaft is configured to rotate around the coupling portion by sliding in the first guide groove in accordance with a movement of the operating lever from a first position of which the operating lever is parallel to a longitudinal axis of the connecting rod inserted into the arm body portion to a second position of which the operating lever is inclined to the longitudinal axis of the connecting rod.

5. The medical manipulator according to claim 4,
wherein the arm operating portion has a coupling rod, a first end of the coupling rod being rotatably connected with the rotating shaft, and a second end of the coupling rod being connected with a proximal end part of the operating wire,
wherein the second end of the coupling rod is moved to the second position side while the operating lever is moved from the first position to the second position, and
wherein the operating wire is pulled by moving the second end of the coupling rod to the second position side.

6. The medical manipulator according to claim 5,
wherein the coupling rod has a positioning portion,
wherein the guide member has a hole which is capable of engaging the positioning portion in a state in which the operating wire is pulled to the arm operating portion side, and
wherein the second bending portion is maintained in a bending state in which the positioning portion is engaged into the hole.

* * * * *